United States Patent [19]
Leenders et al.

[11] Patent Number: 5,710,135
[45] Date of Patent: Jan. 20, 1998

[54] ANTHRACYCLINE PRODRUGS, METHOD FOR PREPARATION AS WELL AS THEIR USE IN SELECTIVE CHEMOTHERAPY

[75] Inventors: Ruben G. G. Leenders, Nijmegen; Eric W. P. Damen, Huissen; Johan Wilhelm Scheeren, Nijmegen; Hidde J. Haisma, Hoevelaken; Pieter H. J. Houba, Utrecht; Dick De Vos, Oegstgeest, all of Netherlands

[73] Assignee: Pharmachemie B.V., Haarlem, Netherlands

[21] Appl. No.: 652,940

[22] Filed: May 24, 1996

[30] Foreign Application Priority Data

Jun. 27, 1995 [EP] European Pat. Off. ............ 95201747

[51] Int. Cl.$^6$ .......................... A61K 31/70; C07H 15/24
[52] U.S. Cl. ..................... 514/34; 536/6.4; 536/18.5; 536/18.6
[58] Field of Search ................... 536/6.4, 18.5, 536/18.6, 536; 514/34

[56] References Cited

FOREIGN PATENT DOCUMENTS

| | | |
|---|---|---|
| 2109304 | 10/1992 | Canada. |
| 0 441 21 A2 | 8/1991 | European Pat. Off.. |
| 0 511 917 A1 | 11/1992 | European Pat. Off.. |
| 0 595 133 A2 | 5/1994 | European Pat. Off.. |
| WO 92/19639 | 11/1992 | WIPO. |

OTHER PUBLICATIONS

Kita et al, Facile and Efficient Syntheses of Carboxylic Anhydrides and Amides Using (Trimethylsilyl) Ethoxyacetylene, J.Org.Chem., vol. 51 No. 22, pp. 4150–4158, Dec. 19, 1985.

Andrianomenjanahary et al, Syntheses of Novel Targeted Pro–Prodrugs of Anthracyclines Potentially Activated by a Monoclonal Antibody Galactosidase Conjugate (Part 1), Biorganic & Medical Chemistry vol. 2, No. 9, pp. 1093–1096, 1992.

Bosslet et al, Tumor–Selective Prodrug Activation by Fusion Protein–Mediated Catalysis, Cancer Reasearch, vol. 54, pp. 2151–2159, Apr. 15, 1994.

Carl et al, Journal of Medical Chemistry, vol. 24, No. 5, May 1981.

Gesson et al, Prodrugs of Anthracycline for Chemotherapy via Enzyme–Monclonal Antibody Conjugates, Anti–Cancer Drug Design, vol. 9, pp. 409–423, 1994.

Jungheim et al, Design of ANtitumor Prodrugs: Substrates for Antibody Targeted Enzymes, Chem. Rev., vol. 94 pp. 1553–1556, Jan. 21, 1994.

Senter et al, Generation of Cytotoxic Agents by Targeted Enzymes, Bioconjugate Chem. vol. 4, pp. 3–9 1993.

Haisma et al, A Monoclonal Antibody–β–Glucuronidase Conjugate as Activator of the Prodrug Epirubicin–Glucuronide for Specific Treatment of Cancer, Br. J. Cancer, vol. 66, pp. 474–478, 1992.

Jungheim et al, Synthesis of Acylhyhydrazido–Substituted Cephemus. Design of Cephalosporin–Vinca Alkaloid Prodrugs: Substrates for an Antibody–Targeted Enzyme, J. Org. Chem. vol. 57, pp. 2334–2340, 1992.

Senter et al, Enhancement of the in Vitro and in Vitro Antitumor Activities of Phosphorylated Mitomycin C and Etoposide Derivativesby Monoclonal Antibod–Alkaline Phosphatase Conjugates, vol. 49, pp. 5789–5792, Nov. 1, 1989.

Senter et al, Anti–Tumor Effects of Antibody–Alkaline Phosphatase Conjugates in Combination with Etopside Phosphate, Proc. Natl. Acad. Sci., vol. 85, pp. 4842–4846, Jul. 1988.

Vingerhoeds et al, A New Application for Liposomes in Cancer Therapy, FEBS, vol. 336, No. 3, pp. 485–490, Dec. 1993.

(List continued on next page.)

*Primary Examiner*—Elli Peselev
*Attorney, Agent, or Firm*—Browdy and Neimark

[57] ABSTRACT

Anthracycline derivatives are disclosed which are coupled to an enzymatically cleavable N-phenyl-O-glycosyl carbamate spacer group, which derivatives are represented by the formula

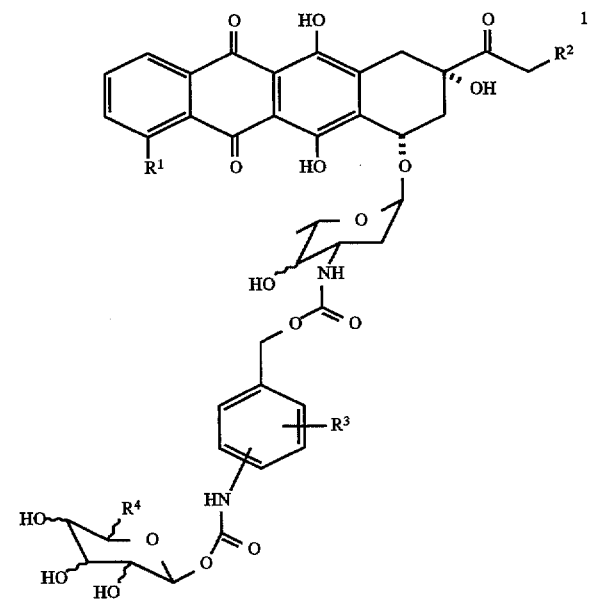

$R^1 = $ —H, —OH, —OMe
$R^2 = $ —H, —OH
$R^3 = $ H, —CX$_3$, —NO$_2$, —CN, —X, —Y, —OY, —NHY, —S(O$_2$)Y, C(O)Y, C(O)OY
$R^4 = $ —CH$_2$OH, C(O)O⁻Z⁺
X = halogen
Y = C$_1$–C$_3$ alkyl, aryl
Z = H, LI, Na, K as well as the acid addition salts thereof.

Further the synthesis of these derivatives and their use, alone or in combination with enzymes or antibody enzyme conjugates are disclosed.

9 Claims, No Drawings

OTHER PUBLICATIONS

Miyashita et al, Prodrug Activation via Catalytic Antibodies, Proc. Natl. Sci. vol. 90, pp. 5337–5340, 1993.

Wallace et al, In Vitro and in Vivo Activities of Monoclonal Antibody–Alkaline Phosphate Conjugates in Combination with Phenol Mustard Phosphatase, Bioconjugate Chem., vol. 2, pp. 349–352, Jun. 24, 1991.

ANTHRACYCLINE PRODRUGS, METHOD FOR PREPARATION AS WELL AS THEIR USE IN SELECTIVE CHEMOTHERAPY

BACKGROUND OF THE INVENTION

This invention relates to novel anthracycline prodrugs, their synthesis and use alone or in combination with enzymes or antibody enzyme conjugates.

The lack of selectivity of cytostatic agents for tumor cells is a serious drawback in conventional cancer chemotherapy. New methods to increase the selectivity of anti-cancer agents are under study and the use of monoclonal antibodies ($M_{ab}$) to target cytotoxicity to tumor cells is one of them. In this context relatively non-toxic prodrugs can be used in cancer treatment which are selectively activated at the tumor site by the action of endogeneous enzymes or targeted enzymes, or via a non-enzymic process.

SUMMARY OF THE INVENTION

The invention relates to anthracycline derivatives coupled to an enzymatically cleavable N-phenyl-O-glycosyl-carbamate spacer group, said anthracycline derivative having formula 1

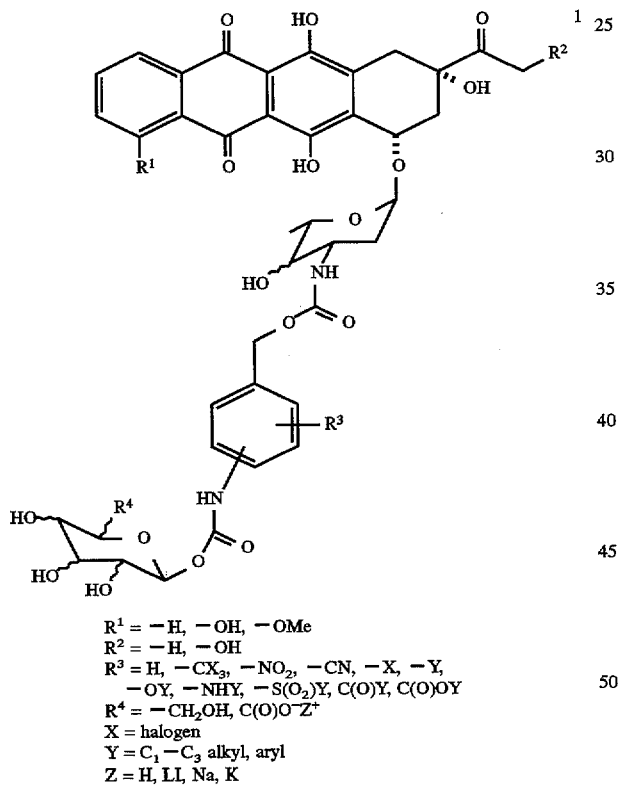

$R^1 = $ —H, —OH, —OMe
$R^2 = $ —H, —OH
$R^3 = $ H, —$CX_3$, —$NO_2$, —CN, —X, —Y, —OY, —NHY, —S($O_2$)Y, C(O)Y, C(O)OY
$R^4 = $ —$CH_2OH$, C(O)O$^-$$Z^+$
X = halogen
Y = $C_1$–$C_3$ alkyl, aryl
Z = H, Li, Na, K as well as the acid addition salts thereof.

The invention therefore also relates to an anthracycline derivative having formula 1 wherein $R^1$, $R^2$, $R^3$, $R^4$, X, Y and Z are defined as above, in the preparation of a medicament for use in a target tissue treatment, wherein the derivative is selectively activated by an enzyme which is coupled to an antibody being specific for the target tissue.

ADEPT (Antibody Directed Enzyme Prodrug Therapy) is a therapy in which an antibody targets an enzyme to the tumor site. After the enzyme has been situated into the tumor, the relatively non-toxic prodrug having formula 1 is given which is converted to the parent drug by action of the enzyme.

Alternatively, the derivative having formula 1 can be activated by an endo- or exogeneous enzyme.

DETAILED DESCRIPTION OF THE INVENTION

It is observed that anthracyclines having an enzymatically cleavable N-phenyl-O-glycosyl carbamate pro-moiety can be converted to anthracyclines having general formula 2

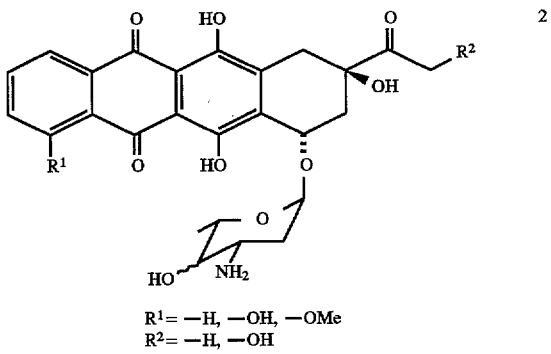

$R^1 = $ —H, —OH, —OMe
$R^2 = $ —H, —OH wherein $R^1$ is —H, —OH, —$OCH_3$, and $R^2$ is —H, —OH, by the action of certain glycosidases or glycosidases conjugated to i.e. monoclonal antibodies or immunoliposomes (see for example M. H. Vingerhoeds et al. FEBS 1993, 336, 485–490), or by the action of catalytic antibodies (see for example H. Miyashita et al. Proc. Natl. Acad. Sci. USA 1993, 90, 5337–5340).

In literature several approaches towards the use and synthesis of prodrugs in ADEPT have been described (reviews: L. N. Jungheim etal. Chem. Rev. 1994, 94, 1553–1566, P. D. Senter et al. Bioconj. Chem. 1993, 4, 3–9). Major limitations of the reported prodrugs are a too slow activation by the concomitant enzyme (H. J. Haisma et al. Br. J. Cancer 1992, 66, 474–478, M. Gerken et al. European patent 1991, 0441218A2), prodrug activation by endogeneous enzymes (P. D. Senter et al. Cancer Res. 1989, 49, 5789–5792 and Proc. Natl. Acad. Sci. USA 1988, 85, 4842–4846, P. M. Wallace etal. Bioconj. Chem. 1991, 2, 349–352) and a too high cytotoxicity of the prodrug (L. N. Jungheim et al. J. Org. Chem. 1992, 57, 2334–2340).

The enzymes to be used for the activation of the present anthracycline derivatives having formula 1 are preferably β-glucuronidase, β-glucosidase and β-galactosidase.

The prodrugs of general formula 1 wherein in the anthracycline part $R^1$ is —H, —OH or —OMe and $R^2$ is —H or —OH, in the spacer part $R^3$ is an hydrogen atom or a group such as —$NO_2$, —$CNCX_3$ or —X (wherein X is an halogen atom), —Y, —OY, —NHY, —S($O_2$)Y, C(O)Y or C(O)OY (wherein Y=$C_1$–$C_3$ alkyl group or an aryl group) and in the sugar part $R^4$ is —$CH_2OH$ or —C(O)O$^-$$Z^+$ (wherein $Z^+$ is a proton or an alkali metal ion such as $Li^+$, $Na^+$, $K^+$) convert to the parent drug of general formula 2 wherein $R^1$ is —H, —OH or —OMe and $R^2$ is —H or —OH upon hydrolysis of the carbohydrate part of the prodrug via the following mechanism (P. L. Carl et al. J. Med. Chem. 1981, 24, 479–480)

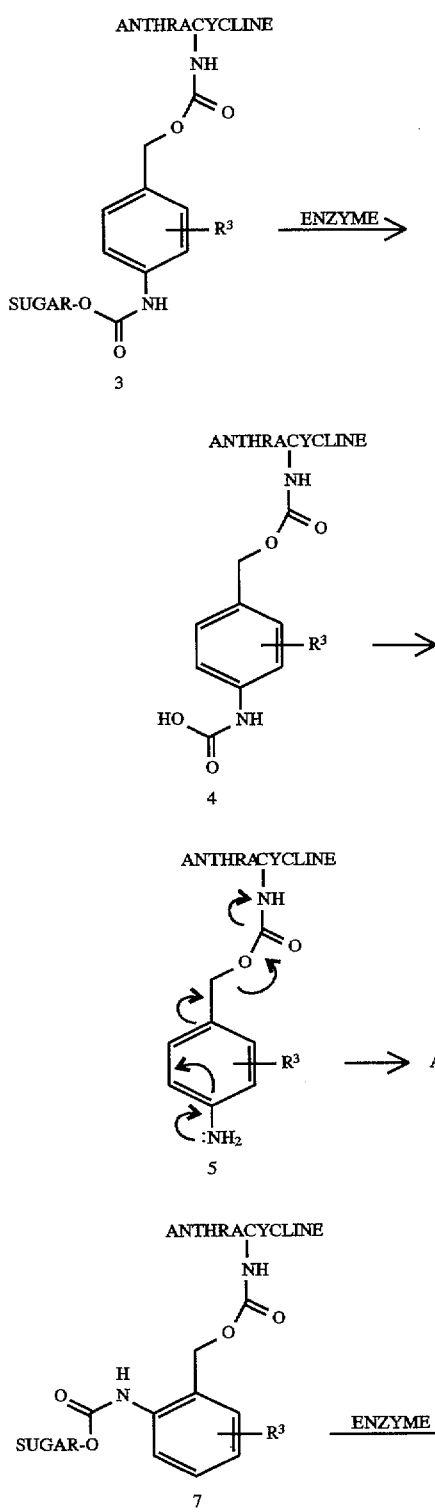

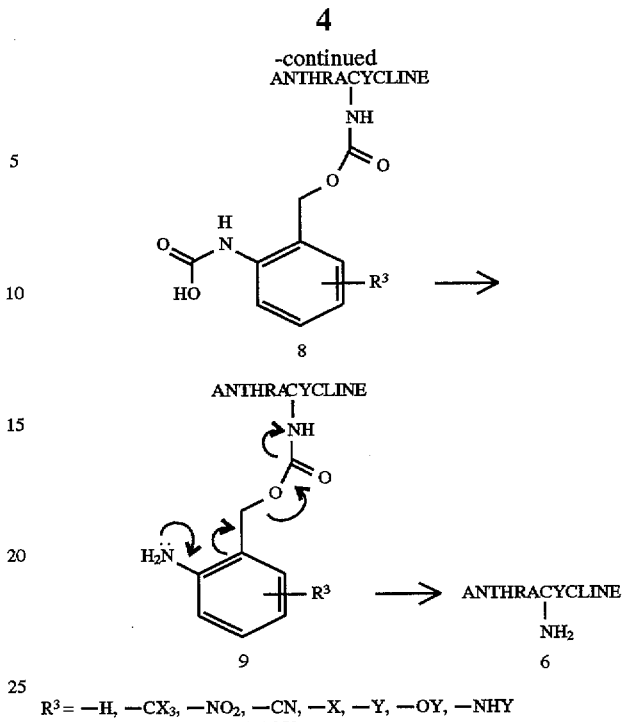

$R^3 = $ —H, —CX$_3$, —NO$_2$, —CN, —X, —Y, —OY, —NHY
—S(O$_2$)Y, C(O)Y, C(O)OY

S = halogen
Y = C$_1$–C$_3$ alkyl, aryl

In contrast to similar prodrugs described by J. Jacquesy et al. WO 92/19639 by K. Bosslet et al. Cancer Res. 1994, 54, 2151–2159, by S. Andrianomenjanahary et al. Bioorg. Med. Chem Lett. 1992, 2, 1093–1096 and by J.-P. Gesson et al. Anti-Cancer Drug Des. 1994, 9, 409–423, the prodrags disclosed in this application having general formula 3 and 7 wherein $R^3$ is an hydrogen atom or a group such as —NO$_2$, —CNCX$_3$ or —X (wherein X is an halogen atom), —Y, —OY, —NHY, —S(O$_2$)Y, C(O)Y or C(O)OY (wherein Y=C$_1$–C$_3$ alkyl group or an aryl group) convert quantitatively to the parent anthracycline cytostatic having the formula 6 without detectable amounts of intermediates 4, 5, 8 or 9. Unsubstituted prodrugs having the formulae 3 and 7 wherein $R^3$ is an hydrogen atom are also converted quantitatively to the parent drug 6 also without detectable intermediates, whereas the analogous prodrugs containing an unsubstituted spacer moiety described by J. Jacquesy et al. WO 92/19639, by K. Bosslet et al. Cancer Res. 1994, 54, 2151–2159, by S. Andrianomenjanahary et al. Bioorg. Med. Chem Lett. 1992, 2, 1093–1096 and by J.-P. Gesson et al. Anti-Cancer Drug Des. 1994, 9, 409–423 did not convert to the parent anthracycline.

SYNTHESIS

The key step in the synthesis of prodrugs having formula 1 (which include 1 para and 1 ortho) is the generation of isocyanates having formulae 11 and 19 respectively at which an anomerically unprotected carbohydrate 12 can be added affording sugar carbamates 13 and 20 respectively (see reaction scheme I and II). As a result of the desired self liquidation potential of the spacer, the sugar carbamate moiety can not be introduced v/a synthetic steps involving intermediates having a free amino group on the spacer because of premature expulsion of the protective group on the benzyl alcohol moiety of the spacer molecule. For this reason the sugar carbamate fragment is introduced in situ, employing the Curtius rearrangement to generate isocyanates as masked carbamates from carboxylic acids of formulae 10 and 18 using diphenylphosphoryl azide. After removal of the silyl protective group of intermediates having formulae 13 and 20 respectively, the benzylic alcohol group of formulae 14 and 21 could be coupled via a carbonyl group to anthracyclines having formula 16 making use of N-succinimidyl chloroformate of formula 15 or p-nitrophenyl chloroformate. Deprotection of the carbohydrate moiety of the compounds having formulae 17 and 22 was easily accomplished using lithium hydroxide in methanol—water.

Alternatively, compounds 1 having a substituted spacer ($R^3$ is not —H) could be synthesized starting from para or ortho substituted toluic acid derivatives 23 or 27 which provide after glucosidation, bromination of the benzylic carbon, and hydrolysis of the benzylic bromide 14 and 21 respectively (see reaction scheme III and IV respectively), which are further transformed to compounds 1 according to reaction scheme I and II respectively.

In contrast to the synthesis of the similar anthracycline derivatives as prodrugs covered by J. Iacquesy et al. WO 92/19639, by K. Bosslet et al. Cancer Res. 1994, 54, 2151–2159, by S. Andrianomenjanahary et al. Bioorg. Med. Chem Lett. 1992, 2, 1093–1096 and by J.-P. Gesson et al. Anti-Cancer Drug Des. 1994, 9, 409–423, the synthesis of the present derivatives having formula 1 is more efficient: The chemical yield and the β-stereoselectivity of the coupling reactions of the anomerically unprotected sugar 12 to isocyanates 11, 19, 24 and 28 are higher in comparison to the yield and α or β-stereoselectivity of the corresponding sugar coupling reactions obtained in the synthesis of the before mentioned similar prodrugs (vide supra).

In contrast to the similar prodrugs reported by J. Jaequesy et al. WO 92/19639, by K. Bosslet et al. Cancer Res. 1994, 54, 2151–2159, by S. Andrianomenjanahary et al. Bioorg. Med. Chem Lett. 1992, 2, 1093–1096 and by J.-P. Gesson et al. Anti-Cancer Drug Des. 1994, 9, 409–423, which require an ortho chloro or ortho nitro substituent on the spacer for optimal activation after enzyme hydrolysis, prodrugs having general formula 1 are all activated to the parent drug after enzyme hydrolysis, including the unsubstituted analogues (wherein $R^3$=—H) . This relates to a smaller amount of synthetic steps to prepare prodrugs 1 (wherein $R^3$=—H) compared with the preparation of the ortho chloro or ortho nitro substituted prodrugs outlined in literature (vide supra). In addition, in the synthesis of prodrugs with general formula 1 having an unsubstituted spacer moiety ($R^1$=—H) , no bromination and no heavy metal salts are involved. This in contrary to the synthesis of the before mentioned ortho chloro or ortho nitro substituted prodrugs.

Reaction scheme I

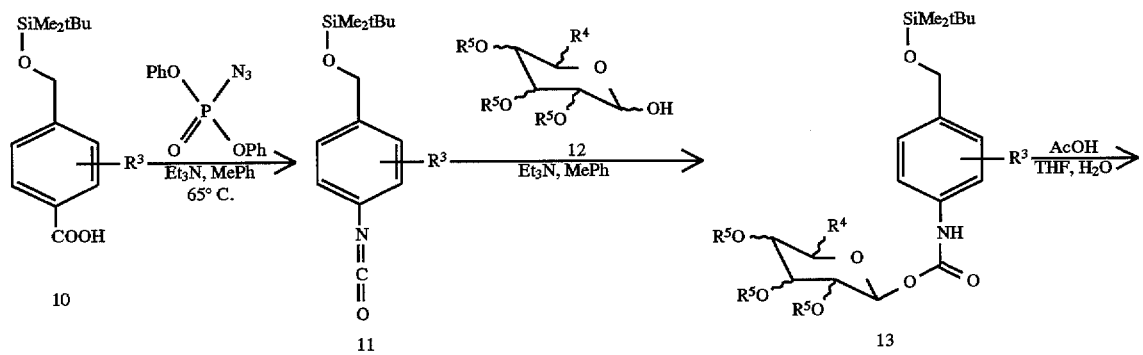

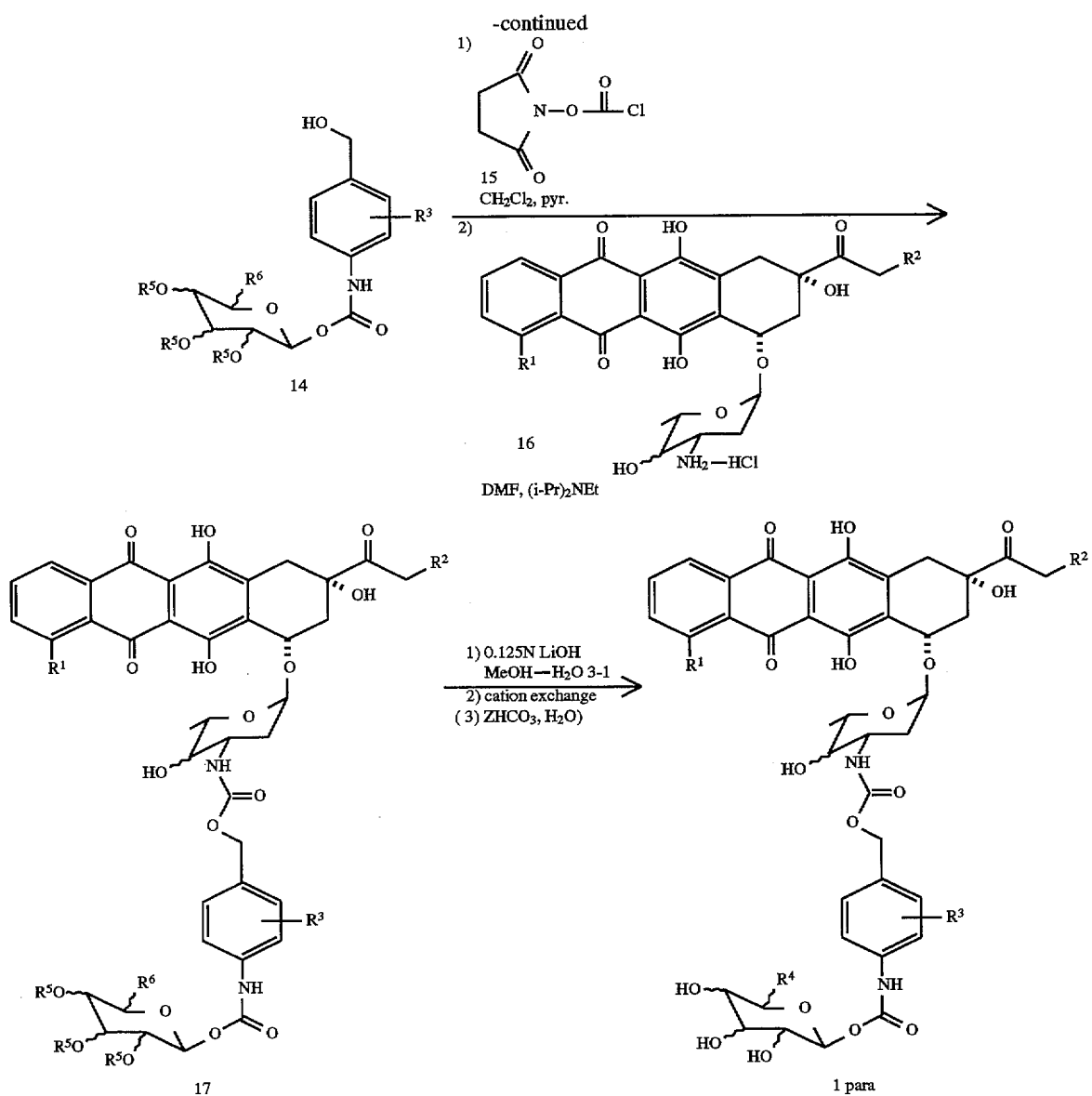
$R^1$ = —H, —OH, —OMe
$R^2$ = —H, —OH
$R^3$ = —H, —CX$_3$, —NO$_2$, —CN, —X, —Y, —OY, —NHY
—S(O$_2$)Y, C(O)Y, C(O)OY
$R^4$ = —CH$_2$OH, C(O)O$^-$Z$^+$
$R^5$ = —φAc
$R^6$ = —CH$_2$OAc, —C(O)OMe
X = halogen
Y = C$_1$–C$_3$ alkyl, aryl
Z = H, Li, Na, K
Reaction scheme II
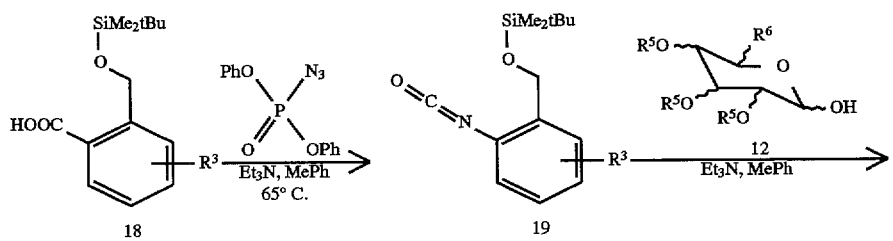

-continued
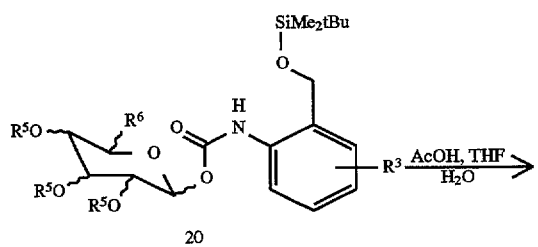
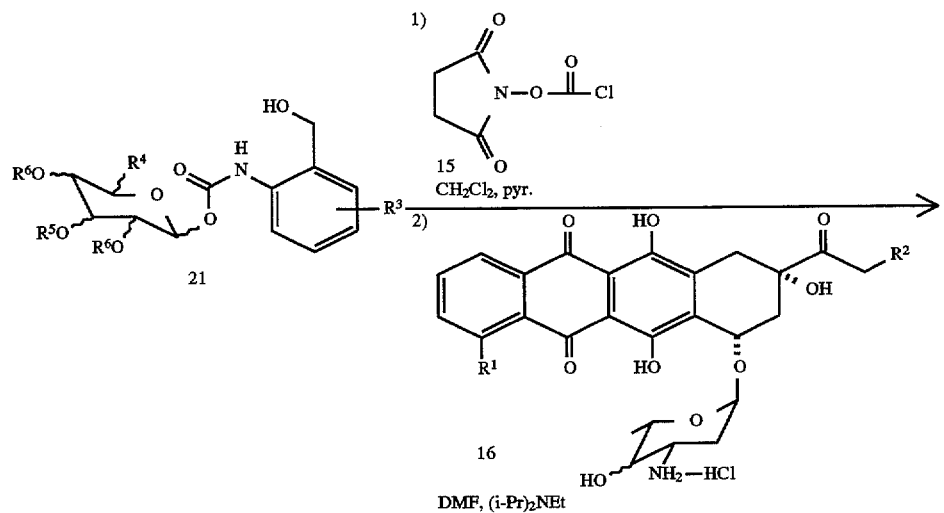
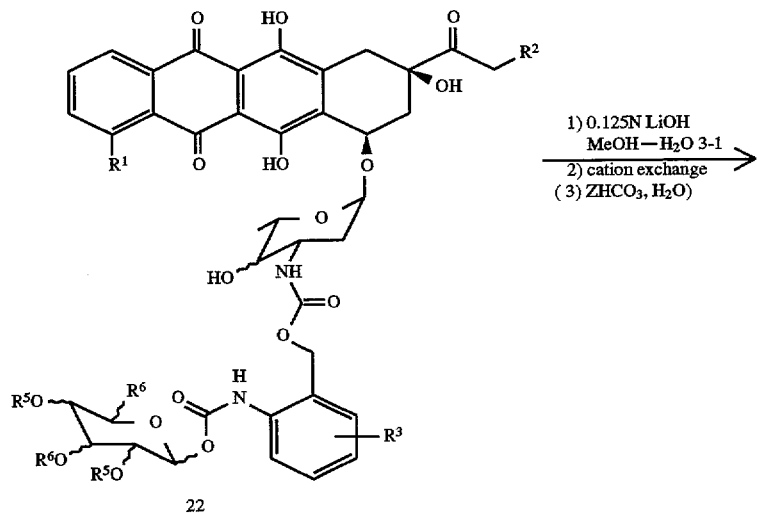

-continued
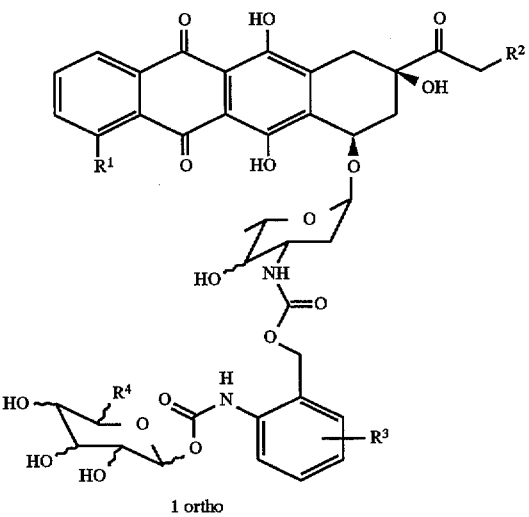
1 ortho
Reaction scheme III
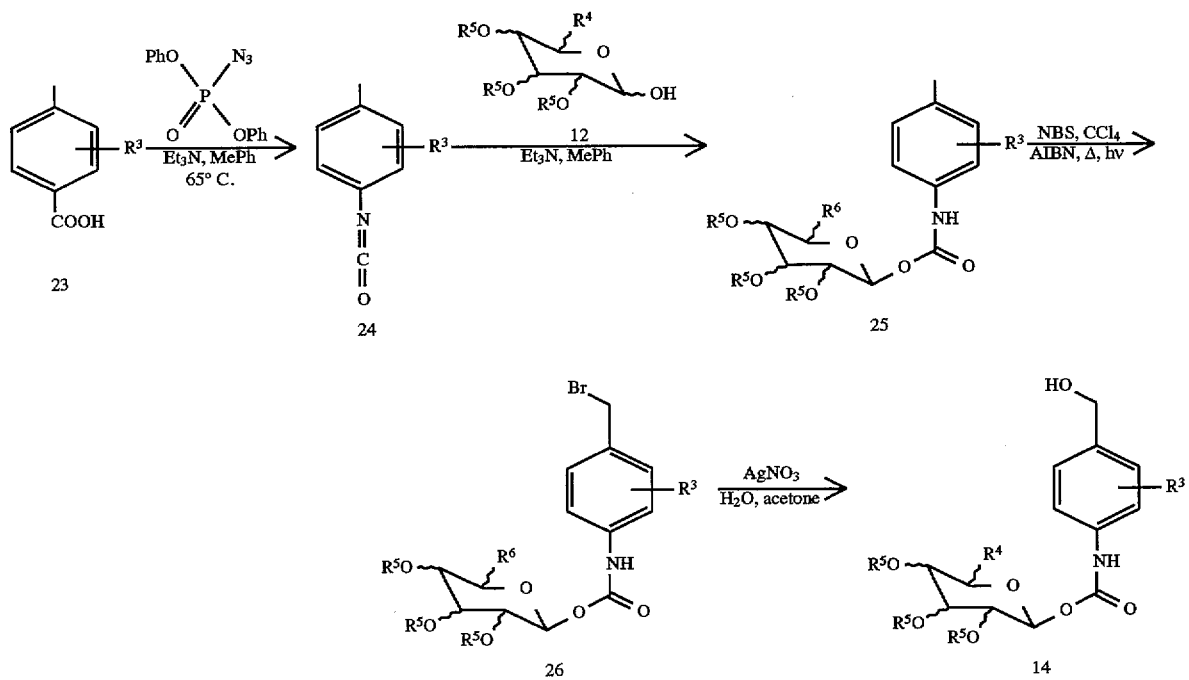
R[1] = —H, —OH, —OMe
R[2] = —H, —OH
R[3] = —H, —CX$_3$, —NO$_2$, —CN, —X, —Y, —OY, —NHY, —S(O$_2$)Y, C(O)Y, C(O)OY
R[4] = —CH$_2$OH, C(O)O$^-$Z$^+$
R[5] = —φAc
R[6] = —CH$_2$OAc, —C(O)OMe
X = halogen
Y = C$_1$–C$_3$ alkyl, aryl
Z = H, Li, Na, K

Reaction scheme IV

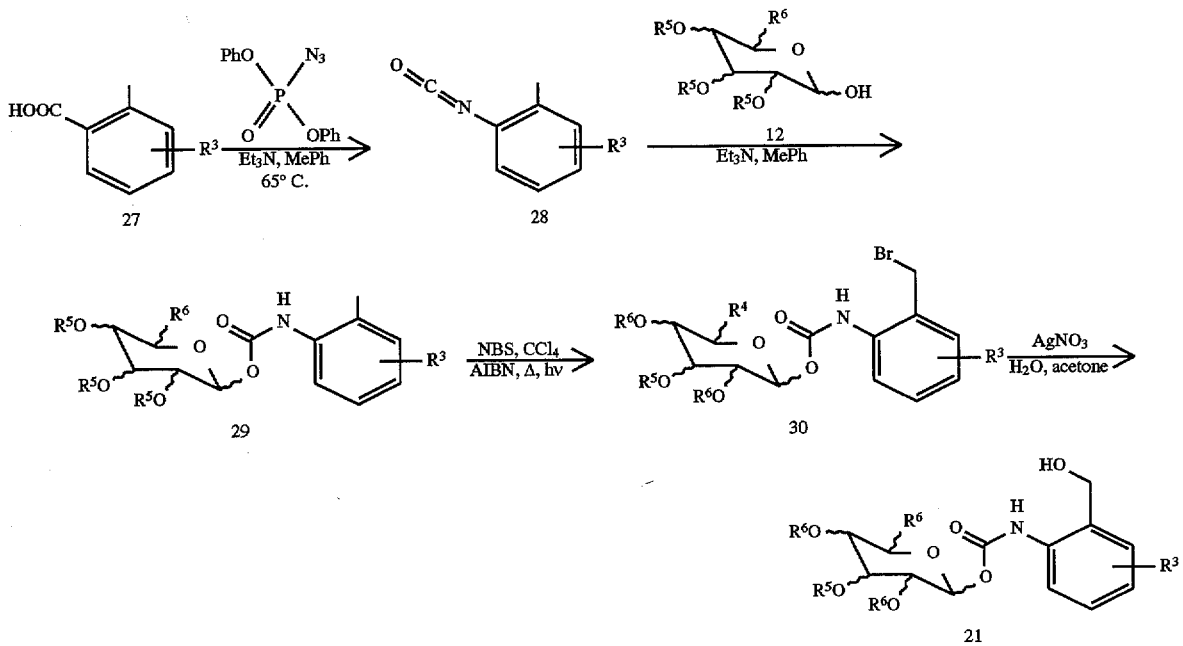

Biological characterization of prodrugs having general formula 1 consists of
- Plasma stability assay
- In vitro cytotoxicity assay, and
- Enzym hydrolysis assay The prodrugs in examples 1 to 6 were all stable in plasma (see example 8).

The prodrugs in examples 1 to 6 were at least 15 times less toxic than the corresponding drugs (see example 8). Enzymatic hydrolysis of the prodrugs is in all cases faster than that of prodrugs having a comparable substitution pattern on the spacer moiety described in literature (J. Jacquesy et al. WO 92/19639, by K. Bosslet et al. Cancer Res. 1994, 54, 2151–2159, by S. Andrianomenjanahary et al. Bioorg. Med. Chem Lett. 1992, 2, 1093–1096 and by J.-P. Gesson et al. Anti-Cancer Drug Des. 1994, 9, 409–423). Furthermore, the spacers were immediately released after glycoside hydrolysis, this in contrast with spacers described in literature (vide supra).

This invention is further explained in the following examples.

EXAMPLE 1

Daunorubicin glucuronide prodrug with unsubstituted para spacer 1a-para ($R^1$=—OMe, $R^2$=—H, $R^3$=—H, $R^4$=—C(O)ONa)

N-[4-(tert-butyldimethylsilyloxymethyl)phenyl] O-(methyl 2,3,4-tri-O-acetyl β-glucuronyl) carbamate 13 ($R^3$=—H)

500 mg (1.88 mmol) of 4-(tert-butyldimethylsilyloxymethyl)benzoic acid 10 (Y. Kita et al. J. Org. Chem. 1986, 22, 4150–4158) was stirred with 486 µL (1.2 eq.) of diphenyl phosphoryl azide and 313 µL (1.2 eq.) of triethylamine in 10 mL of dry toluene under an argon atmosphere. After 12 hours the reaction mixture was stirred at 90° C. for 2 hours. The mixture was cooled to ambient temperature and 331 mg (0.5 eq.) of methyl 2,3,4-tri-O-acetyl glueuronic acid 12 ($R^5$=—Ac, $R^6$=—C(O)OMe) was added. The course of the reaction was followed by means of TLC (SiO$_2$—Et$_2$O). After the glucuronic acid 12 had disappeared, the reaction mixture was diluted with 200 mL of diethylether and washed with 100 mL portions of aqueous 0.5N potassium bisulfate (twice), demineralized water, saturated aqueous sodium bicarbonate and brine succesively. The organic layer was dried over anhydrous sodium sulfate and evaporated. The residual oil was purified by means of column chromatography (SiO$_2$—Et$_2$O/hexane 2/1) to yield 474 mg of N-[4-(tert-butyldimethylsilyloxymethyl)phenyl] O-(methyl 2,3,4-tri-O-acetyl β-glucuronyl) carbamate 13 ($R^3$=—H, $R^5$=—Ac, $R^6$=—C(O)OMe), 79.7 % from 10 ($R^3$=—H) as a white foam, mp 128° C. $^1$H—NMR (100 mHz, CDCl$_3$) δ (ppm)=0.00 (s, 6H, SiMe$_2$—), 0.84 (s, 9H, SiCMe$_3$), 1.95 (s, 9H, OAc), 3.64 (s, 3H, OMe), 4.12 (d, 1H, Gluc5-H, J=9.3 Hz), 4.54 (s, 2 H, ArCH$_2$—), 5.08–5.21 (m, 3H, Gluc2-H Gluc3-H Gluc4-H), 5.68 (d, 1H, Gluc1-H, J=7.9 Hz), 6.63 (s, 1H, NH—), 7.16-7.29 (m, 4H, Ar2-H Ar3-H Ar5-H Ar6-H).

N-[4-(hydroxymethyl)phenyl] O-(methyl 2,3,4-tri-O-acetyl β-glucuronyl) carbamate 14 ($R^3$=—H, $R^5$=—Ac, $R^6$=—C(O)OMe)

766 mg (1.28 mmol) of 13 ($R^3$=—H, $R^5$=—Ac, $R^6$=—C(O)OMe) was stirred in 30 mL of tetrahydrofuran/demineralized water/acetic acid 1/1/1. The course of the deprotection reaction was followed by TLC (SiO$_2$ Et$_2$O). After no starting material could be detected, the reaction mixture was deluted with 200 mL of diethylether and washed with 100 mL portions of demineralized water (3 times), aqueous satureted sodium bicarbonate and with brine succesively. The organic layer was dried over anhydrous sodium sulfate and evaporated. The resulting foam was purified by means of column chromatography ($SiO_2$—EtOAc/hexane 3/1) to afford 457 mg of N-[4-(hydroxymethyl)phenyl] O-(methyl 2,3,4-tri-O-acetyl β-glucuronyl) carbamate 14 ($R^3$=—H, $R^5$=—Ac, $R^6$=—C(O)OMe) as a white foam mp 173° C., 73.9%. $^1$H-NMR (100 mHz, $CDCl_3$) δ (ppm)=1.96 (s, 9H, OAc), 3.64 (s, 3H, OMe), 4.13 (d, 1H, Gluc5-H, J=9.3 Hz), 4.61 (s, 2H, $ArCH_2$—), 5.02–5.31 (m, 3H, Gluc2-H Gluc3-H Gluc4-H), 5.71 (d, 1H, Gluc1-H, J=7.5 Hz), 6.92 (s, 1H, NH), 7.19–7.28 (m, 4H, Ar2-H Ar3-H Ar5-H Ar-6H).

N-[4-(daunorubicin-N-carbonyl-oxymethyl)phenyl] O-(methyl 2,3,4-tri-O-acetyl β-glucuronyl) carbamate 17 ($R^1$=—OMe, $R^2$=—H, $R^5$=—H, $R^5$=—Ac, $R^6$=—C(O)OMe)

300 mg (0.621 mmol) of 14 ($R^3$=—H, $R^6$=—Ac, $R^6$=—C(O)OMe) was stirred with 115 n.g (1.05 eq.) of N-succinimidyl chloroformate 15 and 100 µL (2.0 eq.) of anhydrons pyridine in 25 mL of anhydrous methylene chloride. After no starting material could be detected (TLC $SiO_2$ $Et_2O$), a solution of 420 mg (1.2 eq.) daunorubicin-HCl 16 ($R^1$=—OMe, $R^2$=—H) and 162 µL (1.5 eq.) of diisopropyl ethyl amine in 15 mL of dry N,N-dimethyl formamide was added. The course of the reaction was monitorred by TLC ($SiO_2$—$CH_2Cl_2$/EtOH 10/1). After all of the active ester starting material had disappeared, the reaction mixture was diluted with 200 mL of methylene chloride and washed with 100 mL portions of aqueous 0.5N potassium bisulfate (3 times), demineralized water, aqueous satureted sodium bicarbonate (twice) and with brine. The organic layer was dried over anhydrous sodium sulfate and evaporated. The resulting red residue was purified twice by means of circular chromatography using a chromatotron supplied with a 2 mm silica plate and methylene chloride/ethanol 10/1 and 30/1 respectively. After evaporation of the eluent, the resulting red product was sonicated in diisopropyl ether and filtrated to yield 348 mg of N-[4-(daunorubicin-N-carbonyl-oxymethyl)phenyl]O-(methyl 2,3,4-tri-O-acetyl β-glucuronyl) carbamate 17 ($R^1$=—OMe, $R^2$=—H, $R^3$=—H, $R^5$=—AC, $R^6$=—C(O)OMe), 54.0 % as amorphous red crystals, mp 163°–164° C. $^1$H—NMR (400 mHz, $CDCl_3$) δ (ppm)=1.28 (d, 1H, 5'-Me, J=6.6 Hz), 1.78–1.88 (m, 3H, 2'$_{eq}$-H 2'$_{ax}$-H 4'-OH), 2.05 (s, 9H, OAc), 2.09 (dd, 1H, 8$_{ax}$-H, J=15,2 Hz J=3.7 Hz), 2.30 (d, 1H, 8$_{eq}$-H, J=14.9 Hz), 2.41 (s, 3H, 9-C(O)Me), 2.88 (d, 1H, 10$_{ax}$-H, J=18.8 Hz), 3.20 (d, 1H, 10$_{eq}$-H, J=18.8 Hz), 3.67 (m, 1H, 4'-H), 3.72 (s, 3H, C(O)OMe), 3.88 (m, 1H, 3'-H), 4.05 (s, 3H, 4-OMe), 4.15–4.25 (m, 2H, 5'-H Gluc5-H), 4.48 (s, 1H, 9—OH), 4.89 (d, 1H, ArCH$_a$H$_b$—, J=12.2 Hz), 4.95 (d, 1H, ArCH$_a$H$_b$—, J=12.2 Hz), 5.15–5.30 (m, 4H, Gluc3-H Gluc4-H 7-H 3'-NH-), 5.38 (t, 1H, Gluc3—H, J=9.3 Hz), 5.47 (d, 1H, 1'-H, J=3.1 Hz), 5.77 (d, 1H, Gluc1-H, J=8.0 Hz), 7.18 (d, 2H, ArH-3 ArH-5, J=8.0 Hz), 7.20–7.30 (m, 3H, Ar2-H Ar6-H ArNH—), 7.37 (d, 1H, 3—H, J=8.4 Hz), 7.76 (t, 1H, 2-H, J=8.0 Hz), 8.00 (d, 1H, 1—H, J=7.7 Hz), 13.22 (s, 1H, 11-OH), 13.94 (s, 1H, 6-OH).

N-[4-(daunorubicin-N-carbonyl-oxymethyl)phenyl] O-β-glucuronyl carbamate sodium salt 1a-para ($R^1$=—OMe, $R^2$=—H, $R^3$=—H, $R^4$=—C(O)ONa)

To 297 mg (0.289 mmol) of 17 ($R^2$=—OMe, $R^2$=—H, $R^3$=—H, $R^5$=—Ac, $R^6$ =—C(O)OMe) was added 13.8 mL (6 eq.) of a 0.125N lithium hydroxyde solution in methanol/demineralized water 3/1, the resulting deep blue solution was stirred at 0° C. under an argon atmosphere. Progress of the deprotection was monitorred on reversed phase TLC ($SiO_2$-$C_{18}$ MeCN/$H_2O$ 1/1). After completion of the reaction, the reaction mixture was diluted with 10 mL of demineralized water and neutralized by adding ca. '10 g of amberlite cation exchange material ($H^+$ form). 10 mL of tetrahydrofuran was added to homogenize the suspension, the amberlite was removed by filtration and ca 150 mg sodium bicarbonate was added. The water layer was deluted to ca. 100 mL and washed with 200 mL portions of chloroform (twice). After phase separation, the chloroform suspended in the water layer was removed by evaporation and the red aqueous product solution was transferring it to a reversed phase column packed with RP-$C_{18}$ material and eluted with 300 mL of demineralized water to remove the exess of sodium bicarbonate. The column was succesively washed with acetonitrile/demineralized water 4/1 to elute the product and the acetonitrile was removed by evaporation. Freeze drying of the aqueous product solution afforded 214 mg of N-[4-(daunombicin-N-carbonyl-oxymethyl) phenyl] O-β-glucuronyl carbamate sodium salt 1a-para ($R^1$=—OMe, $R^2$=—H, $R^3$=—H, $R^4$=—C(O)ONa), 81.4% as a red fluffy solid mp 175° C. (dec.). $C_{42}H43N_2O_{20}Na$ 4 $H_2O$ calculated C 50.91%, H 5.19%, N 2.83%, measured C 50.73%, H 4.96%, N 2.94%. $^1$H-NMR (400 mHz, DMSO-$d_6$) δ (ppm)=1.11 (d, 3H, 5'-Me, J=6.6Hz), 1.47(dd, 1H, 2'$_{eq}$-H, J=12.1Hz J=3.4 Hz), 1.82 (dt, 1H, 2'$_{ax}$-H, J=11.5 Hz J=3.4 Hz), 2.07 (dd, 1H, 8$_{ax}$-H, J=14.1 Hz J=6.1 Hz), 2.19 (dd, 1H, 8$_{eq}$-H, J=14.1 J=3.1 Hz), 2.27 (s, 3H, 9-C(O)Me), 3.11 (d, 1H, 10$_{eq}$-H, J=18.5 Hz), 3.13 (d, 1H, 10$_{ax}$-H, J=18.5 Hz), 3.20–3.65 (m, 4H, 4'-H Gluc2-H Gluc3-H Gluc4-H), 3.71 (m, 1H, 3'-H), 3.95 (s, 3H, 4-OMe), 4.16 (q, 1H, 5'-H, J=6.6 Hz), 4.70 (d, 1H, 4'-OH, J=5.1 Hz), 4.76–5.32 (m, 4H, Gluc5-H Gluc2-OH Gluc3-OH Gluc4-OH), 4.84 (d, 1H, ArCH$_a$H$_b$—, J=12.8 Hz), 4.88 (d, 1H, ArCH$_a$H$_b$—, J=12.8 Hz), 4.90 (t, 1H, 7-H, J=5.1 Hz), 5.20 (d, 1H, 1'-H, J=3.0 Hz), 5.28 (d, 1H, Gluc1-H, J=8.2 Hz), 5.52 (s, 1H, 9-OH), 6.84 (d, 1H, 3'-NH-, J=8.0 Hz), 7.23 (d, 2H, Ar3-H Ar5-H, J=8.4 Hz), 7.43 (d, 2H, Ar2-H Ar6—H, J=8.4 Hz), 7.69. (dd, 1H, 3—H, J=6.8 Hz J=3.0 Hz), 7.82–7.89 (m, 2H, 1-H 2-H), 9.90 (s, 1H, ArNH—) 13.25 (s, 1H, 11-OH), 13.99 (s, 1H, 6-OH).

EXAMPLE 2

Daunorubicin glucuronide prodrug with unsubstituted ortho spacer 1a-ortho ($R^1$=—OMe, $R^2$=—H, $R^4$=—H, $R^4$=—C(O)ONa)

N-[2-(tert-butyldimethylsilyloxymethyl)phenyl] O-(methyl 2,3,4-tri-O-acetyl β-glucuronyl) carbamate 20 ($R^3$=—H, $R^5$=—Ac, $R^6$=C(O)OMe)

400 mg (1.50 mmol) of 2-(tert-butyldimethylsilyloxymethyl)benzoic acid 18 ($R^3$=—H) was stirred with 389 µL (1.2 eq.) of diphenyl phosphoryl azide and 250 µL (1.2 eq.) of triethylamine in 10 mL of dry toluene under an argon atmosphere. After 12 hours the reaction mixture was stirred at 90° C. for 2 hours. The mixture was cooled to ambient temperature and 250 mg (0.5 eq.) of methyl 2,3,4-tri-O-acetyl glueuronie acid 12 ($R^5$=—Ac, $R^6$=—C(O)OMe) was added. The course of the reaction was followed by means of TLC ($SiO_2$—$Et_2O$). After the glucuronic acid 12 had disappeared, the reaction mixture was diluted with 200 mL of diethylether and washed with 100 mL portions of aqueous 0.5N potassium bistfifate (twice), demineralized water, saturated aqueous sodium bicarbonate and brine succesively. The organic layer was dried over anhydrous sodium sulfate and evaporated. The residual oil was purified by means of column chromatography ($SiO_2$—$Et_2O$/hexane 2/1) to yield 310 mg of N-[2-(tert-butyldimethylsilyloxymethyl)phenyl] O-(methyl 2,3,4-tri-O-acetyl β-glucuronyl) carbamate 20 ($R^3$=—H, $R^5$=—Ac, $R^6$=—C(O)OMe), 69.2% from 18 ($R^3$=—H). $^1$H-NMR (100 mHz, CDCl$_3$) δ (ppm)=0.00 (s, 3H, SiMe$_a$Me$_b$—), 0.05 (s, 3H, SiMe$_a$Me$_b$—), 0.83 (s, 9H, SiCMe$_3$), 1.96 (s, 9H, OAc), 3.66 (s, 3H, OMe), 4.16 (d, 1H, Gluc5—H, J=9.4 Hz), 4.60 (d, 1H, ArCH$_a$H$_b$—, J=18.1 Hz), 4.72 (d, 1H, ArCH$_a$H$_b$—, J=18.1 Hz), 5.01–5.32 (m, 3H, Gluc2-H Gluc3-H Gluc4-H), 5.76 (d, 1H, Gluc1-H, J=7.8 Hz), 6.94–7.32 (m, 3H, Ar3-H Ar4-H Ar5-H), 7.90 (d, 1H, Ar6-H, J=8.0 Hz), 8.61 (s, 1H, ArNH—).

N-[2-(hydroxwmethyl)phenyl] O-(methyl 2,3,4-tri-O-acetyl β-glucuronyl) carbamate 21 ($R^3$=—H, $R^5$= —Ac, $R^6$=—C(O)OMe)

310 mg (0.52 mmol) of 20 ($R^3$=—H, $R^5$=—Ac, $R^6$=—C(O)OMe) was stirred in 30 mL of tetrahydrofuran/ demineralized water/acetic acid 1/1/1. The course of the aleprotection reaction was followed by TLC (SiO$_2$ Et$_2$O). After no starting material could be detected, the reaction mixture was diluted with 200 mL of diethylether and washed with 100 mL portions of demineralized water (3 times), aqueous saturated sodium bicarbonate and with brine succesively. The organic layer was dried over anhydrous sodium sulfate and evaporated. The resulting foam was purified by means of column chromatography (SiO$_2$—EtOAc/hexane 3/1) to afford 171 mg of N-[2-(hydroxymethyl)phenyl] O-(methyl 2,3,4-tri-O-acetyl β-glucuronyl) carbamate 21 ($R^3$=—H, $R^5$=—Ac, $R^6$=—C(O)OMe) as a white foam mp 132° C., 68.2%. $^1$H-NMR (100 mHz, CDCl$_3$) δ (ppm)=1.96 (s, 9H, OAc), 3.64 (s, 3H, OMe), 4.11 (d, 1H, Gluc5-H, J=9.4Hz), 4.59 (s, 2H, ArCH$_2$—), 5.09–5.21 (m, 3H, Gluc2-H Gluc3-H Gluc4-H), 5.74 (d, 1H, Gluc1—H, J=7.5 Hz), 6.96–7.31 (m, 3H, Ar3-H Ar4-H Ar5-H), 7.70 (d, 1H, Ar6—H, J=7.7 Hz), 8.15 (s, 1H, ArNH—).

N-[2-(daunorubicin-N-carbonyl-oxymethyl)phenyl] O-(methyl 2,3,4-tri-O-acetyl βglucuronyl) carbamate 22 ($R^1$=—OMe, $R^2$=—H, $R^5$=—H, $R^6$= —Ac, $R^6$=—C(O)OMe)

100 mg (0.213 mmol) of 21 ($R^3$=—H, $R^5$=—Ac, $R^6$=—C(O)OMe) was stirred with 44 mg (1.05 eq.) of p-nitrophenyl chloroformate 15 and 21 μL (1.05 eq.) of anhydrous pyridine in 10 mL of anhydrous methylene chloride. After no starting material could be detected (TLC SiO$_2$ Et$_2$O), a solution of 144 mg (1.2 eq.) daunorubicin-HCl 16 ($R^1$=—OMe, $R^2$=—H) and 73 μL (2 eq.) of diisopropyl ethyl amine in 10 mL of dry N,N-dimethyl formamide was added. The course of the reaction was monitorred by TLC (SiO$_2$—CH$_2$Cl$_2$/EtOH 10/1). After all of the active ester starting material had disappeared, the rection mixture was diluted with 200 mL of methylene chloride and washed with 100 mL portions of aqueous 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate and methylene chloride/ethanol 20/1 and 25/1 respectively. After evaporation of the eluent, the resulting rod product was sonicated in diisopropyl ether and filtrated to yield 133 mg of N-[2-(daunorubicin-N-carbonyl-oxymethyl)phenyl] O-(methyl 2,3,4-tri-O-acetyl β-glucuronyl) carbamate 22 ($R^1$=—OMe, $R^2$=—H , $R^3$=—H, $R^5$=—Ac, $R^6$=—C(O)OMe), 62.2% as amorphous red crystals mp 151°–153° C. $^1$H—NMR (400 mHz, CDCl$_3$) δ (ppm)=1.30 (d, 3H, 5'-Me, J=6.5 Hz), 1.80–1.85 (m, 3H, 2'$_{eq}$-H 2'$_{ax}$-H 4'-OH) 2.00 (s, 3H, OAc) 2.04 (s, 3H, OAc), 2.05 (s, 3H, OAc), 2.16 (dd, 1H, 8$_{ax}$-H, J=14.8 Hz J=4.1 Hz), 2.33 (d, 1H, 8$_{eq}$—H, J=15.2 Hz), 2.43 (s, 3H, 9-C(O)Me), 2.95 (d, 1H, 10$_{ax}$-H, J=18.9 Hz), 3.23 (d, 1H, 10$_{eq}$-H, J=18.9 Hz), 3.67 (d, 1H, 4'-H, J=6.7 Hz), 3.72 (s, 3H, C(O)OMe), 3.90 (m, 1H, 5'-H), 4.07 (s, 3H, 4-OMe), 4.20–4.25 (m, 2H, 3'-H Gluc5-H), 4.46 (s, 1H, 9-OH), 4.96 (d, 1H, ArCH$_a$H$_b$—, J=12.6 Hz), 5.07 (d, 1H, ArCH$_a$H$_b$—, J=12.6 Hz), 5.16 (t, 1H, Gluc2—H, J=8.0 Hz), 5.25–5.35 (m, 4H, 7-H 3'-NH- Gluc3-H Gluc4-H), 5.50 (m, 1H, 1'-H), 5.80 (d, 1H, Gluc1-H, J=7.52), 7.08 (t, 1H, Ar4—H, J=7.4 Hz), 7.26 (d, 1H, Ar3—H, J=8.8 Hz), 7.32 (t, 1H, Ar5-H, J=7.7 Hz), 7.39 (d, 1H, 3—H, J=8.5 Hz), 7.78 (t, 1H, 2—H, J=8.1 Hz), 7.84 (m, 1H, Ar6-H), 8.03 (d, 1H, 1—H, J=7.7 Hz), 8.20 (s, 1H, ArNH—), 13.28 (s, 1H, 11-OH), 13.97 (s, 1H, 6-OH).

N-[2-(daunorubicin-N-carbonyl-oxymethyl)phenyl] O-β-glucuronyl carbamate sodium salt 1a-ortho ($R^1$=—OMe, $R^2$=—H, $R^3$=—H, $R^4$=—C(O)ONa)

To 20 mg (19 μmol) of 22 ($R^1$=—OMe, R2=—H, $R^3$=—H, $R^5$=—Ac, $R^6$=—C(O)OMe) was added 0.31 mL (6 eq.) of a 0.125N lithium hydroxyde solution in methanol/demineralized water 3/1, the resulting deep blue solution was stirred at 0° C. under an argon atmosphere. Progress of the deprotection was monitorred on reversod phase TLC (SiO$_2$—C$_{18}$MeCN/H$_2$O 1/1). After completion of the reaction, the reaction mixture was diluted with 5 mL of demineralized water and 2 mL of tetrahydrofuran, and neutralized by adding ca. 2 g of amberlite cation exchange material (H$^+$form). The amberlite is removed by filtration and ca 15 mg sodium bicarbonate was added. The water layer was washed with 100 mL portions of methylene chloride (twice). After phase separation, the methylene chloride suspended in the water layer was removed by evaporation and the red aqueous product solution was transferring it to a reversed phase column packed with RP—C$_{18}$ material and eluted with 300 mL of demineralized water to remove the excess of sodium bicarbonate. The column was succesively washed with acetonitrile/demineralized water 4/1 to elute the product and the acetonitrile was removed by evaporation. Freeze drying of the aqueous product solution afforded 12.2 mg of N-[2-(daunombicin-N-carbonyl-oxymethyl)phenyl] O-β-glucuronyl carbamate sodium salt 1a-ortho ($R^1$=—OMe, $R^2$=—H, $R^3$=—H, $R^4$=—C(O)ONa), 68.8% as a red fluffy solid, mp 171° C. (dec.). C$_{42}$H$_{43}$N$_2$O$_{20}$Na 3 HO calculated C 51.85%, H 5.08%, N 2.88%, measured C 51.36%, H 4.86%, N 2.69%. $^1$H-NMR (400 mHz, DMSO-d$_6$) δ (ppm)=1.12 (d, 3H, 5'-Me, J=6.4 Hz), 1.46 (dd, 1H, 2'$_{eq}$-H, J=12.6 Hz), 1.85 (dt, 1H, 2'$_{ax}$-H, J=12.6 Hz J=3.5 Hz), 2.11 (dd, 1H, 8$_{ax}$-H, J=14.4 Hz J=5.8 Hz), 2.20 (d, 1H, 8$_{eq}$-H, J=14.4 Hz), 2.26 (s, 3H, 9-C(O)Me), 2.93 (d, 1H, 10$_{eq}$-H, J=18.2 Hz), 2.99 (d, 1H, 10$_{ax}$-H, J=18.2 Hz), 3.15–3.65 (m, 4H, 4'-H Gluc2-H Gluc3-H Gluc4-H), 3.72 (m, 1H, 3'-H), 3.99 (s, 3H, 4-OMe), 4.17 (q, 1H, 5'-H, J=6.4 Hz), 4.7–4.90 (m, 2H, 4'-OH, Gluc5-H), 4.94 (t, 1H, 7-H, J=4.4 Hz), 4.98 (s, 2H, ArCH$_2$—), 5.19–5.24 (m, 2H, 2 Gluc-OH), 5.22 (d, 1H, 1'-H, J=3.1 Hz), 5.32 (d, 1H, Gluc—OH, J=5.5 Hz), 5.34 (d, 1H, Gluc1-H, J=8.0 Hz), 5.55 (s, 1H, 9-OH), 7.03 (d, 1H, 3'-NH—, J=8.0 Hz), 7.15 (t, 1H, Ar4—H, J=7.3), 7.27 (t, 1H, Ar5—H, J=7.7), 7.33 (d, 1H, Ar3—H, J=7.6 Hz), 7.40 (d, 1H, Ar6—H, J=7.8 Hz), 7.66 (dd, 1H, 3-H, J=5.9 Hz J=3.9 Hz), 7.88–7.94 (m, 2H, 1-H 2-H), 9.25 (s, 1H, ArNH—) 13.29 (s, 1H, 11-OH), 14.04 (s, 1H, 6-OH).

EXAMPLE 3

Doxorubicin glucuronide prodrug with unsubstituted para spacer 1b-para ($R^1$=—OMe, $R^2$= —OH, $R^3$=—H, $R^4$=—C(O)ONa)

N-[4-(doxorubicin-N-carbonyl-oxymethyl)phenyl] O-(methyl 2,3,4-tri-O-acetyl β-glucuronyl) carbamate 17 ($R^1$=—OMe, $R^2$=—OH, $R^3$=—H, $R^5$=—Ac, $R^6$=—C(O)OMe)

25 mg (52 μmol) of 14 ($R^3$=—H, $R^5$=—Ac, $R^6$=—C(O)OMe) (vide supra) was stirred with 10 mg (1.05 eq.) of N-succinimidyl chloroformate 15 and 9 μL (2.0 eq.) of anhydrous pyridine in 3 mL of anhydrous methylene chloride. After no starting material could be detected (TLC SiO$_2$ Et$_2$O), a solution of 45 mg (1.5 eq.) doxorubicin-HCl 16 (R$^1$=—OMe, R$^2$=—OH) and 23 μL (2.5 eq.) of diisopropyl ethyl amine in 5 mL of dry N,N-dimethyl formamide was added. The course of the reaction was monitorred by TLC (SiO$_2$—CH$_2$Cl$_2$/EtOH 10/1). After all of the active ester starting material had disappeared, the reaction mixture was diluted with 200 mL of methylene chloride and washed with 100 mL portions of aqueous 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate using methylene chloride/ethanol 20/1 as eluent. After evaporation of the eluent, the resulting red product was sonicated in diisopropyl ether and filtrated to yield 35 mg of N-[4-(doxorubicin-N-carbonyl-oxymethyl)phenyl] O-(methyl 2,3,4-tri-O-acetyl β-glucuronyl) carbamate 17 (R$^1$=—OMe, R$^2$=—OH, R$^3$=—H, R$^5$=—Ac, R$^6$=—C(O)OMe), 66.7% as amorphous red crystals mp 165°–167° C. $^1$H—NMR (400 mHz, CDCl$_3$) δ (ppm)=1.28 (d, 3H, 5'-Me, J=6.5 Hz), 1.75–1.90 (m, 3H, 2'$_{eq}$-H2'$_{ax}$-H4'-OH), 2.05 (s, 9H, OAc), 2.14 (dd, 1H, 8$_{ax}$-H, J=14.7 Hz J=3.9 Hz), 2.32 (d, 1H, 8$_{eq}$-H, J=14.7 Hz), 2.97 (d, 1H, 10$_{ax}$-H, J=18.9 Hz), 6.06 (s, 1H, 14-OH), 3.24 (d, 1H, 10$_{eq}$-H, J=18.9 Hz), 3.66 (m, 1H, 4'-H), 3.72 (s, 3H, C(O)OMe), 3.86 (m, 1H, 3'-H), 4.06 (s, 3H, 4-OMe), 4.13 (q, 1H, 5'-H, J=6.5 Hz), 4.22 (d, 1H, Gluc5-H, J=9.7 Hz), 4.55 (s, 1H, 9-OH), 2.75 (s, 2H, 9-C(O)CH$_2$—), 4.93 (d, 1H, ArCH$_a$H$_b$—, J=12.4 Hz), 4.96 (d, 1H, ArCH$_a$H$_b$-, J=12.4 Hz), 5.15–5.30 (m, 4H, 7-H 3'-NH- Gluc3-H Gluc4-H), 5.36 (t, 1H, Gluc3—H, J=9.3 Hz), 5.48 (d, 1H, 1'-H, J=3.0 Hz), 5.77 (d, 1H, Gluc1-H, J=8.0 Hz), 7.20 (d, 2H, Ar3-H Ar5-H, J=7.0 Hz), 7.20–7.35 (m, 3H, Ar2-H Ar6-H ArNH—), 7.38 (d, 1H, 3—H, J=8.5 Hz), 7.78 (t, 1H, 2—H, J=8.0 Hz), 8.01 (d, 1H, 1—H, J=7.8 Hz), 13.19 (s, 1H, 11-OH), 13.93 (s, 1H, 6-OH).

N-[4-(doxorubicin-N-carbonyl-oxymethyl)phenyl] O-β-glucuronyl carbamate sodium salt 1b-para (R$^1$=—OMe, R$^2$=—OH, R$^3$=—H, R$^4$=—C(O)ONa)

10.0 mg (9.5 μmol) of 17 (R$^2$=—OMe, R$^2$=—OH, R$^3$=—H, R$^6$=—Ac, R$^5$=—C(O)OMe) was dissolved in 0.46 mL (6 eq.) of a 0.125N lithium hydroxyde solution in methanol/demineralized water 3/1 and cooled to 0° C. The resulting deep blue solution was stirred at 0° C. under an argon atmosphere. Progress of the aleprotection was monitorred on reversed phase TLC (SiO$_2$—C$_{18}$MeCN/H$_2$O 1/1). After completion of the reaction, the reaction mixture was diluted with 10 mL of demineralized water and neutralized by adding ca. 2 g of umberlite cation exchange material (H$^+$ form). The amberlite is removed by filtration and ca 15 mg sodium bicarbonate was added. The water layer was washed with 100 mL portions of methylene chloride (twice). After phase separation, the methylene chloride suspended in the water layer was removed by evaporation and the red aqueous product solution was transferring it to a reversed phase column packed with RP-C$_{18}$ material and eluted with 300 mL of demineralized water to remove the exess of sodium bicarbonate. The column was successively washed with 20 mL of acetonitrile/demineralized water 1/1 to elute the product and the acetonitrile was removed by evaporation. Freeze drying of the aqueous product solution afforded 5.3 mg of N-[4-(doxorubicin-N-carbonyl-oxymethyl)phenyl] O-β-glucuronyl carbamate sodium salt 1b-para (R$^1$=—OMe, R$^2$=—OH, R$^3$=—H, R$^4$=—C(O)ONa), 60.0% as a red fluffy solid. mp 191° C. (dec.). C$_{42}$H$_{43}$N$_2$O$_{21}$Na 5 H$_2$O calculated C 49.22%, H 5.21%, N 2.73%, measured C 49.05%, H 4.67%, N 2.60%. $^1$H-NMR (400 mHz, DMSO-d$_6$) δ (ppm)=1.12 (d, 3H, 5'-Me, J=6.3 Hz), 1.47 (d, 1H, 2'$_{eq}$-H, J=12.3 Hz), 1.83 (dt, 1H, 2'$_{ax}$-H, J=12.9 Hz J=3.5 Hz), 2.12 (dd, 1H, 8$_{ax}$-H, J=14.2 Hz J=5.6 Hz), 2.20 (d, 1H, 8$_{eq}$-H, J=11.9 Hz), 2.95 (d, 1H, 10$_{eq}$-H, J=18.8 Hz), 3.01 (d, 1H, 10$_{ax}$-H, J=18.8 Hz), 3.05–3.60 (m, 4H, 4'-H Gluc2-H Gluc3-H Gluc4-H), 3.71 (m, 1H, 3'-H), 3.99 (s, 3H, 4-OMe), 4.15 (q, 1H, 5'-H, J=6.3 Hz), 4.57 (s, 2H, 14-H$_2$), 4.62–4.71 (m, 1H, Gluc5-H), 4.68 (d, 1H, 4'-OH, J=4.9 Hz), 4.80–5.30 (m, 4H, 14-OH Gluc2-OH Gluc3-OH Gluc4-OH), 4.88 (s, 2H, ArCH$_2$—), 4.94 (t, 1H, 7-H, J=4.2 Hz), 5.21 (d, 1H, 1'-H, J=2.7 Hz), 5.33 (d, 1H, Gluc1-H, J=8.0 Hz), 5.46 (s, 1H, 9-OH), 6.83 (d, 1H, 3'-NH-, J=8.0 Hz), 7.24 (d, 2H, Ar3-H Ar5—H, J=8.1 Hz), 7.43 (d, 2H, Ar2-H Ar6—H, J=8.1 Hz), 7.65 (t, 1H, 3-H, J=4.8 Hz), 7.88–7.94 (m, 2H, 1-H 2-H), 9.91 (s, 1H, ArNH—) 13.28 (s, 1H, 11-OH), 14.03 (s, 1H, 6-OH).

EXAMPLE 4

Idarubicin glucuronide prodrug with unsubstituted para spacer 1c-para (R$^1$=—H, R$^2$=—H, R$^3$=—H, R$^4$=—C(O)ONa)

N-[4-(idarubicin-N-carbonyl-oxymethyl)phenyl] O-(methyl 2,3,4-tri-O-acetyl β-glucuronyl) carbamate 17 (R$^1$=—H, R$^3$=—H, R$^5$=—H, R$^5$=—Ac, R$^6$=—C(O)OMe)

100 mg (0.207 mmol) of 14 (R$^3$=—H, R$^5$=—Ac, R$^6$=—C(O)OMe) (vide supra) was stirred with 37 mg (1.05 eq.) of N-succinimidyl chloroformate 15 and 36 μL (2.0 eq.) of anhydrous pyridine in 10 mL of anhydrous methylene chloride. After no starting material could be detected (TLC SiO)$_2$ Et$_2$O), a solution of 121 mg (1.1 eq.) idarubicin-HCl 16 (R$^1$=—H, R$^2$=—H) and 90 μL 2.5 eq.) of diisopropyl ethyl amine in 25 mL of dry N,N-dimethyl formamide was added. The course of the reaction was monitorred by TLC (SiO$_2$—CH$_2$Cl$_2$/EtOH 10/1). After all of the active ester starting material had disappeared, the reaction mixture was diluted with 200 mL of methylene chloride and washed with 100 mL portions of aqueons 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate using methylene chloride/ethanol 20/1 and 25/1 respectively as eluent. After evaporation of the eluent, the resulting red product was sonicated in diisopropyl either and filtrated to yield 171 mg of N-[4-(idarubicin-N-carbonyloxymethyl) phenyl] O-(methyl 2,3,4-tri-O-acetyl β-glucuronyl) carbamate 17 (R$^1$=—H, R$^2$=—H, R$^3$=—H, R$^5$=—Ac, R$^6$=—C(O)OMe), 80.8% as amorphous red crystals mp 156°–157° C.

N-[4-(idarubicin-N-carbonyl-oxymethyl)phenyl] O-β-glucuronyl carbamate sodium salt 1c-para (R$^1$=—H, R$^2$=—H, R$^3$=—H, R$^4$=—C(O)ONa)

15.3 mg (15.2 μmol) of 17 (R$^1$=—H, R$^2$=—H, R$^3$=—H, R$^5$=—Ac, R$^6$ =—C(O)OMe) was dissolved in 0.73 mL (6 eq.) of a 0.125N lithium hydroxyde solution in methanol/demineralized water 3/1 and cooled to 0° C. The resulting deep blue solution was stirred at 0° C. under an argon atmosphere. Progress of the aleprotection was monitorred on reversed phase TLC (SiO$_2$—C$_{18}$MeCN/H$_2$O 1/1). After completion of the reaction, the reaction mixture was diluted with 10 mL of demineralized water and neutralized by adding ca. 2 g of amberlite cation exchange material (H$^+$ form). The amberlite is removed by filtration and ca 15 mg sodium bicarbonate was added. The water layer was washed with 100 mL portions of methylene chloride (twice). After phase separation, the methylene chloride suspended in the water layer was removed by evaporation and the red aqueous product solution was transferring it to a reversed phase column packed with RP-$C_{18}$ material and eluted with 300 mL of demineralized water to remove the exess of sodium bicarbonate. The column was succesively washed with 20 mL of acetonitrile/demineralized water 1/1 to elute the product and the acetonitrile was removed by evaporation. Freeze drying of the aqueous product solution afforded 10.4 mg of N-[4-(idambicin-N-carbonyl-oxymethyl)phenyl] O-β-glucuronyl carbamate sodium salt 1c-para ($R^1$=—H, $R^2$=—H, $R^3$=-H, $R^4$=—C(O)ONa), 78.5% as a red fluffy solid. $C_{41}H_{41}N_2O_{19}$Na 3 $H_2O$ calculated C 52.23%, H 5.02%, N 2.97%, measured C 52.48%, H 4.87%, N 2.84%. $^1$H-NMR (400 mHz, DMSO-$d_6$) δ (ppm)=1.12 (d, 3H, 5'-Me, J=6.3 Hz), 1.48 (d, 1H, $2'_{eq}$-H, J=12.6 Hz), 1.84 (dt, 1H, $2'_{ax}$-H, J=12.6 Hz J=3.4 Hz), 2.12 (dd, 1H, $8_{ax}$-H, J=14.3 Hz J=5.7 Hz), 2.22 (d, 1H, $8_{eq}$-H, J=14.3), 2.27 (s, 3H, 9-C(O)Me), 2.96 (d, 1H, $10_{eq}$-(H, J=18.4 Hz), 3.03 (d, 1H, $10_{ax}$-H, J=18.4 Hz), 3.20–3.65 (m, 4H, 4'-H Gluc2-H Gluc3-H Gluc4-H), 3.73 (m, 1H, 3'-H), 4.18 (q, 1H, 5'-H, J=6.3 Hz), 4.71 (d, 1H, 4'-OH, J=5.5 Hz), 4.75–4.85 (m, 1H, gluc5-H), 4.87 (s, 2H, ArCH$_2$—), 4.95 (t, 1H, 7—H, J=4.6 Hz), 5.22 (d, 1H, 1'-H, J=2.6 Hz), 5.17–5.33 (m, 3H, Gluc2-OH Gluc3-OH Gluc4-OH), 5.35 (d, 1H, Gluc1-H, J=8.1 Hz), 5.58 (s, 1H, 9-OH), 6.85 (d, 1H, 3'-NH-, J=7.9 Hz), 7.24 (d, 2H, Ar3-H Ar5-H, J=8.2 Hz), 7.43 (d, 2H, Ar2-H Ar6-H, J=8.2 Hz), 7.95–8.02 (m, 2H, 2-H 3-H), 8.26–8.33 (m, 2H, 1-H 4-H), 9.94 (s, 1H, ArNH—) 13.35 (s, 1H, 11-OH), 13.54 (s, 1H, 6-OH).

EXAMPLE 5

Daunorubicin glucoside prodrug with unsubstituted para spacer 1d-para ($R^1$=—OMe, $R^2$=—H, $R^3$=—H, $R^4$=—CH$_2$OH)

N-[4-(tert-butyldimethylsilyloxymehtyl)phenyl] O-(2,3,4,6-tetra-O-acetyl β-glucosyl) carbamate 13 ($R^3$=—H, $R^5$=—Ac, $R^6$=—CH$_2$OAc)

250 mg (0.94 mmol) of 4-(tert-butyldimethylsilyloxymethyl)benzoic acid 10 ($R^3$=—H) was stirred with 243 μL (1.2 eq.) of diphenyl phosphoryl azide and 157 μL (1.2 eq.) of triethylamine in 15 mL of dry toluene under an argon atmosphere. After 12 hours the reaction mixture was stirred at 90° C. for 2 hours. The mixture was cooled to ambient temperature and 219 mg (0.67 eq.) of 2,3,4,6 -tetra-O-acetyl glucose 12 ($R^5$=—Ac, $R^6$=—CH$_2$OAc) was added. The course of the reaction was followed by means of TLC (SiO$_2$—Et$_2$O). After the glucose 12 had disappeared, the reaction mixture was diluted with 200 mL of diethylether and washed with 100 mL portions of aqueous 0.5N potassium bisulfate (twice), demineralized water, saturated aqueous sodium bicarbonate and brine succesively. The organic layer was dried over anhydrous sodium sulfate and evaporated. The residual oil was purified by means of column chromatography (SiO$_2$—Et$_2$O/hexane 2/1) to yield 240 mg of N-[4-(tert-butyldimethylsilyloxymethyl)phenyl] O-(2,3,4,6-tetra-O-acetyl β-gluosyl) carbamate 13 ($R^3$=—H, $R^5$=—Ac, $R^6$=—CH$_2$OAc), 62.7% from 10 ($R^3$=—H), as a white foam. $^1$H-NMR (100 mHz, CDCl$_3$) δ (ppm) =0.00 (s, 6H, SiMe$_2$—), 0.84 (s, 9H, SiCMe$_3$), 1.95 (s, 3H, OAc), 1.96 (s, 3 H, OAc), 1.97 (s, 3H, OAc), 2.00 (s, 3H, OAc), 3.70–3.85 (m, 1H, Gluc5-H), 4.02 (dd, 1 H, Gluc6—H$_a$H$_b$—, J=12.4 Hz, J=2.0), 4.26 (dd, 1H, Gluc6-H$_a$H$_b$—, J=12.4 Hz J=4.3 Hz), 4.60 (s, 2H, ArCH$_2$—), 5.00–5.30 (m, 3H, Gluc2-H Gluc3-H Gluc4-H), 5.67 (d, 1H, Gluc1-H, J=7.8 Hz), 6.85 (s, 1H, ArNH—), 7.15–7.40 (m, 4H, Ar2-H Ar3-H Ar5-H Ar6-H).

N-[4-(hydroxymethyl)phenyl] O-(2,3,4,6-tetra-O-acetyl β-glucosyl) carbamate 14 ($R^3$=—H, $R^5$=—Ac, $R^6$=—CH$_2$OAc)

240 mg (0.394 mmol) of 13 ($R^3$=—H, $R^5$=—Ac, $R^6$=—CH$_2$OAc) was stirred in 30 mL of tetrahydrofuran/ demineralized water/acetic acid 1/1/1. The course of the deprotection reaction followed by TLC (SiO$_2$ Et$_2$O). After no starting material could be detected, the reaction mixture was deluted with 200 mL of diethylether and washed with 100 mL portions of demineralized water (3 times), aqueous saturated sodium bicarbonate and with brine succesively. The organic layer was dried over anhydrous sodium sulfate and evaporated. The resulting foam was purified by means of column chromatography (SiO$_2$—EtOAc/hexane 3/1 ) to afford 132 mg of N-[4-(hydroxymethyl)phenyl] O-(2,3,4,6-tetra-O-acetyl β-glucosyl) carbamate 14 ($R^3$=—H, $R^5$=—Ac, $R^6$=—CH$_2$OAc), 67.6% $^1$H-NMR (100 mHz, CDCl$_3$) δ (ppm)=1.91 (s, 3H, OAc), 1.92 (s, 3H, OAc), 1.94 (s, 3 H, OAc), 1.96 (s, 3H, OAc), 3.70–3.85 (m, 1H, Gluc5-H), 3.98 (dd, 1H, Gluc6-H$_a$H$_b$—, J=12.4 Hz, J=2.0), 4.22 (dd, 1H, Gluc6-H$_a$H$_b$—, J=12.4 Hz J=4.3 Hz), 4.54 (s, 2H, ArCH$_2$—), 4.90–5.20 (m, 3H, Gluc2-H Gluc3-H Gluc4-H), 5.62 (d, 1H, Gluc1-H, J=7.8 Hz), 6.93 (s, 1H, ArNH—), 7.15–7.25 (m, 4H, Ar2-H Ar3-H Ar5-H Ar6-H).

N-[4-(daunorubicin-N-carbonyl-oxymethyl)phenyl] O-(2,3,4,6-tetra-O-acetyl β-glucosyl) carbamate 17 ($R^1$=—OMe, $R^2$=—H , $R^3$=—H, $R^5$=—Ac, $R^6$=—CH$_2$OAc)

80 mg (0.161 mmol) of 14 ($R^3$=—H, $R^5$=—Ac, $R^6$=—CH$_2$OAc) was stirred with 34 mg (1.05 eq.) of p-nitrophenyl chloroformate and 16 μl (1.2 eq.) of anhydrous pyridine in 10 mL of anhydrous methylene chloride. After no starting material could be detected (TLC SiO$_2$ Et$_2$O), a solution of 108 mg (1.2 eq.) daunorubicin-HCl 16 ($R^1$=—OMe, $R^2$=—H) and 56 μL (2.0 eq.) of diisopropyl ethyl amine in 10 mL of dry N,N-dimethyl formamide was added. The course of the reaction was monitorred by TLC (SiO$_2$—CH$_2$Cl$_2$/EtOH 10/1). After all of the active ester starting material had disappeared, the reaction mixture was diluted with 200 mL of methylene chloride and washed with 100 mL portions of aqueous 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate using methylene chloride/ethanol 20/1 as eluent. After evaporation of the eluent, the resulting red product was sonieated in diisopropyl ether and filtrated to yield 97 mg of N-[4-(daunombicin-N-carbonyl-oxymethyl)phenyl] O-(2,3,4,6-tetra-O-acetyl-β-glucosyl) carbamate 17 ($R^1$=—OMe, $R^2$=—H, $R^3$=—H, $R^5$=—Ac, $R^6$=—CH$_2$OAc), 57.5% as amorphous red crystals mp 145°–148° C. $^1$H-NMR (400 mHz, CDCl$_3$) δ (ppm)=1.29 (d, 1H, 5'-Me, J=6.5 Hz), 1.70–1.95 (m, 3H, $2'_{eq}$-H $2'_{ax}$-H 4'-OH), 2.02 (s, 3H, OAc), 2.04 (s, 6H, OAc), 2.07 (s, 3H, OAc), 2.11 (dd, 1H, $8_{ax}$-H, J=14.8 Hz J=3.9 Hz), 2.31 (d, 1H, $8_{eq}$-H, J=14.8 Hz), 2.41 (s, 3H, 9-C(O)Me), 2.91 (d, 1H, $10_{ax}$-H, J=18.7 Hz), 3.22 (d, 1H, $10_{eq}$-H, J=18.7 Hz), 3.65 (m, 1H, 4'-H), 3.85–3.95 (m, 2H, 3'-H Gluc5-H), 4.07 (s, 3H, 4-OMe), 4.12 (d, 1H, Gluc6-H$_a$H$_b$-, J=11.7 Hz), 4.21 (q, 1H, 5'-H, J=6.5 Hz), 4.31 (dd, 1H, Gluc6-H$_a$H$_b$—, J=11.7 Hz J=4.6 Hz), 4.48 (s, 1H, 9-OH), 4.92 (d, 1H, ArCH$_a$H$_b$-, J=12.2 Hz), 4.97 (d, 1H, ArCH$_a$H$_b$—, J=12.2 Hz), 5.10–5.35 (m, 5H, 7-H 3'-NH- Gluc2-H Gluc3-H Gluc4-H), 5.48 (d, 1H, 1'-H, J=3.3 Hz), 5.75 (d, 1H, Gluc1-H, J=8.1 Hz), 7.10 (s, 1H, ArNH—), 7.22

(d, 2H, ArH-3 ArH-5, J=7.9 Hz), 7.31 (d, 2H, Ar2-H Ar6—H, J=7.9 Hz), 7.38 (d, 1H, 3—H, J=8.6 Hz), 7.78 (t, 1H, 2—H, J=8.0 Hz), 8.02 (d, 1H, 1—H, J=7.5 Hz), 13.26 (s, 1H, 11-OH), 13.96 (s, 1H, 6-OH).

N-[4-(daunorubicin-N-carbonyl-oxymethyl)phenyl] O-β-glucosyl carbamate 1d-para ($R^1$=—OMe, $R^2$=—H, $R^3$=—H, $R^4$=—$CH_2OH$)

12.5 mg (11.9 μmol) of 17 ($R^1$=—OMe, $R^2$=—H, $R^3$=—H, $R^5$=—Ac, $R^6$=—$CH_2OAc$) was dissolved in 0.57 mL (6 eq.) of a 0.125N lithium hydroxyde solution in methanol/demineralized water 3/1 and cooled to 0° C. The resulting deep blue solution was stirred at 0° C. under an argon atmosphere. Progress of the deprotection was monitorred on reversed phase TLC ($SiO_2$-$C_{18}$ MeCN/$H_2O$ 1/1). After completion of the reaction, the reaction mixture was diluted with 5 mL of demineralized water and neutralized by adding ca. 2 g of amberlite cation exchange material ($H^+$ form). The amberlite is removed by filtration and the water layer was deluted to 100 mL and washed with 100 mL portions of methylene chloride (twice). After phase separation, the methylene chloride suspended in the water layer was removed by evaporation and the resulting red aqueous product suspension was homogenized by adding ca. 10% acetonitrile. The red solution was transferred to a reversed phase column packed with RP-$C_{18}$ material and the column was eluted with 300 mL of acetonitrile/demineralized water 1/4 to remove impurities. The column was succesively washed with 20 mL of acetonilrile/demineralized water 1/1 to elute the product and the acetonitrile was removed by evaporation. Freeze drying of the aqueous product solution afforded 8.7 mg of N-[4-(daunorubicin-N-carbonyl-oxymethyl)phenyl] O-β-glucosyl carbamate 1d-para ($R^1$=—OMe, $R^2$=—H, $R^3$=—H, $R^4$=—$CH_2OH$), 79.3% as a red fluffy solid mp 182°–184° C. $C_{42}H_{46}N_2O_{19}$ 2 $H_2O$ calculated C 54.90%, H 5.48%, N 2.05%, measured C 54.45%, H 5.24%, N 2.88%. $^1$H—NMR (400 mHz, DMSO-$d_6$) δ (ppm) =-0.06 (s, 4H, Gluc2-OH Gluc3-OH Gluc4-OH, Gluc6-OH), 1.13 (d, 3H, 5'-Me, J=6.5 Hz), 1.47 (d, 1H, 2'$_{eq}$-H, J=12.8 Hz), 1.83 (dt, 1H, 2'$_{ax}$-H, J=12.8 Hz J=3.5 Hz), 2.08 (dd, 1H, 8$_{ax}$-H, J=14.4 Hz J=5.4 Hz), 2.20 (d, 1H, 8$_{eq}$-H, J=14.4 Hz), 2.27 (s, 3H, 9-C(O)Me),2.93 (s, 2H, Gluc6-Hz), 3.00–3.80 (m, 10H, 10$_{eq}$-H, 10$_{ax}$-H, 3'-H, 4'-H, 9-OH, 4'-OH, Gluc2-H Gluc3-H Gluc4-H, Gluc5-H), 3.97 (s, 3H, 4-OMe), 4.17 (q, 1H, 5'-H, J=6.5 Hz), 4.87 (s, 2H, ArCH$_2$—), 4.92 (t, 1H, 7-H, J=4.4 Hz), 5.21 (d, 1H, 1'-H, J=2.6 Hz), 5.35 (d, 1H, Gluc1-H, J=8.2 Hz), 6.83 (d, 1H, 3'-NH-, J=8.0 Hz), 7.24 (d, 2H, Ar3-H Ar5-H, J=8.3 Hz), 7.42 (d, 2H, Ar2-H Ar6—H, J=8.3 Hz), 7.62 (dd, 1H, 3—H, J=6.2 Hz J=—3.5 Hz), 7.85–7.90 (m, 2H, 1-H 2-H), 9.88 (s, 1H, ArNH—) 13.26 (s, 1H, 11-OH), 14.00 (s, 1H, 6-OH).

EXAMPLE 6

Daunorubicin glucuronide prodrug with 2-nitro substitited para spacer 1e-para ($R^1$=—OMe, $R^2$=—H, $R^3$=—2-$NO_2$, $R^4$=—C(O)ONa)

N-(4-methyl 2-nitrophenyl) O-(methyl 2,3,4-tri-O-acetyl β-glucuronyl) carbamate 25 ($R^3$=-2-$NO_2$, $R^5$=—Ac, $R^6$=—C(O)OMe)

100 mg (0.56 mmol) of commercially available 4-methyl-2-nitrophenyl isocyanate 24 ($R^3$=-2-$NO_2$) was dissolved in 10 mL of dry toluene under an argon atmosphere and cooled to 0° C. 100 mg (0.5 eq.) of methyl 2,3,4-tri-O-acetyl glucuronic acid 12 ($R^5$=—Ac, $R^6$=—C(O)OMe) and one drop of triethylamine were added. The course of the reaction was followed by means of TLC ($SiO_2$—$Et_2O$). After the glueuronic acid 12 had disappeared, the reaction mixture was diluted with 200 mL of diethylether and washed with 100 mL portions of aqueous 0.5N potassium bisulfate (twice), demineralized water, saturated aqueous sodium bicarbonate and brine succesively. The organic layer was dried over anhydrous sodium sulfate and evaporated. The residue was sonieated in 10 mL of $Et_2O$/hexane 2/1 and filtrated to yield 207 mg (89%) of N-(4-methyl 2-nitrophenyl) O-(methyl 2,3,4-tri-O-acetyl β-glucuronyl) carbamate 25 ($R^3$=-2-$NO_2$, $R^5$=—Ac, $R^6$=—C(O)OMe)

N-[4-(bromomethyl) 2-nitrophenyl] O-(methyl 2,3,4-tri-O-acetyl β-glucuronyl) carbamate 26 ($R^3$=-2-$NO_2$, $R^5$=—Ac, $R^6$=—C(O)OMe)

100 mg (0.19 mmol) of 25 ($R^3$=-2-$NO_2$, $R^5$=—Ac, $R^6$=—C(O)OMe) was dissolved in 20 mL of tetrachloro methane and 41 mg (1.2 eq.) of N-bromosuccinimide and a catalytic amount of AIBN were added. The solution was heated to reflux for 2 hours and after cooling, the reaction mixture was filtrated, evaporated and dried under reduced pressure (0.1 mm Hg). The crude N-[4-(bromomethyl) 2-nitrophenyl] O-(methyl 2,3,4-tri-O-acetyl β-glucuronyl) carbamate 26 ($R^3$=-2-$NO_2$, $R^5$=—Ac, $R^6$=—C(O)OMe) was used in the next step without further purification.

N-[4-(hydroxymethyl) 2-nitrophenyl] O-(methyl 2,3,4-tri-O-acetyl β-glucuronyl) carbamate 14 ($R^3$=-2-$NO_2$, $R^5$=—Ac, $R^6$=—C(O)OMe)

89 mg (0.15 mmol) of 26 ($R^3$=-2-$NO_2$, $R^5$=—Ac, $R^6$=—C(O)OMe) was dissolved in 5 mL of acetone and 5 mL (3 eq.) of 0.1N aqueous silver nitrate were added. The reaction mixture was stirred overnight, filtrated and evaporated. The resulting oil was redissolved in methylene chloride, washed with brine and dried over sodiumsulfate. After the methylene chloride had been evaporated, the crude reaction mixture was purified by column chromatography ($SiO_2$, diethyl ether/hexane 10/1) to furnish 64 mg (81%) of N-(4-hydroxymethyl 2-nitrophenyl) O-(methyl 2,3,4-tri-O-acetyl β-glucuronyl) carbamate 14 ($R^3$=-2-$NO_2$, $R^5$=—Ac, $R^6$=—C(O)OMe).

N-[4-(daunorubicin-N-carbonyl-oxymethyl) 2-nitrophenyl] O-methyl 2,3,4-tri-O-acetyl β-glucuronyl) carbamate 17 ($R^1$=—OMe, $R^2$=—H, $R^3$=-2-$NO_2$, $R^5$=—Ac, $R^6$=—C(O)OMe)

50 mg (0.095 mmol) of 14 ($R^3$=-2-$NO_2$, $R^5$=—Ac, $R^6$=—C(O)OMe) was stirred with 18 mg (1.05 eq.) of N-succinimidyl chloroformate 15 and 9 μL (1.2 eq.) of anhydrous pyridine in 5 mL of anhydrous methylene chloride. After no starting material could be detected (TLC $SiO_2$ $Et_2O$), a solution of 64 mg (1.2 eq.) daunorubicin-HCl 16 ($R^1$=—OMe, $R^2$=—H) and 33 μL (2 eq.) of diisopropyl ethyl amine in 15 mL of dry N,N-dimethyl formamide were added. The course of the reaction was monitorred by TLC ($SiO_2$—$CH_2Cl_2$/EtOH 10/1). After all of the active ester starting material had disappeared, the reaction mixture was diluted with 200 mL of methylene chloride and washed with 100 mL portions of aqueous 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate and methylene chloride/ethanol 20/1 and 25/1 respectively. After evaporation of the eluent, the resulting red product was sonicated in diisopropyl ether and filtrated to yield 78 mg of N-[4-(daunombicin-N-carbonyl-oxymethyl) 2-nitrophenyl] O-(methyl 2,3,4-tri-O-acetyl β-glucuronyl) carbamate 17 ($R^1$=—OMe, $R^2$=—H, $R^3$=-2-$NO_2$, $R^5$=—Ac, $R^6$=—C(O)OMe), 76% as amorphous red crystals.

N-[4-(daunorubicin-N-carbonyl-oxymethyl)2-nitrophenyl] O-β-glucuronyl carbamate sodium salt 1e-para ($R^1$=—OMe, $R^2$=—H, $R^3$=-2-$NO_2$, $R^4$=—C(O)ONa)

50 mg (0.046 mmol) of 17 ($R^1$=—OMe, $R^2$=—H, $R^3$=-2-$NO_2$, $R^5$=—Ac, $R^6$=—C(O)OMe) was dissolved in 2.22 mL (6 eq) of 0.125N LiOH in methanol/demineralized water 3/1 and cooled to 0° C. The resulting deep blue solution was stirred at 0° C. under an argon atmosphere, progress of the deprotection was monitorred on reversed phase TLC ($SiO_2$—$C_{18}$MeCN/$H_2O$ 1/1). After completion of the reaction, the reaction mixture was diluted with 10 mL of demineralized water and neutralized by adding ca. 2 g of amberlite cation exchange material ($H^+$ form). The amberlite was removed by filtration and ca 20 mg sodium bicarbonate was added. The red aqueous product solution was transferred to a reversed phase column packed with RP-$C_{18}$ material and eluted with 300 mL of demineralized water to remove the exess of sodium bicarbonate. The column was succesively washed with 20 mL of acetonitrile/demineralized water 1/4 to elute the product and the acetonitrile was removed by evaporation. Freeze drying of the aqueous product solution afforded 37 mg (83%) of N-[4-(daunorubicin-N-carbonyl-oxymethyl) 2-nitrophenyl] O-β-glucuronyl carbamate sodium salt 1e-para ($R^1$=—OMe, $R^2$=—H, $R^3$=-2-$NO_2$, $R^4$=—C(O)ONa) as a red fluffy solid.

EXAMPLE 7

Daunorubicin galactose prodrug with unsubstituted para spacer 1f-para ($R^1$=—OMe, $R^2$=—H, $R^3$=—H, $R^4$=—$CH_2OH$)

N-[4-(tert-butyldimethethysilyloxymethyl)phenyl] O-(2,3,4,6-tetra-O-acetyl β-galactosyl) carbamate 13 ($R^3$=—H, $R^5$=—Ac, $R^6$=—$CH_2OAc$)

218 mg (0.82 mmol) of 4-(tert-butyldimethylsilyloxymethyl)benzoic acid 10 ($R^3$=—H) was stirred with 195 µL (1.1 eq.) of diphenyl phosphoryl azide and 125 µL (1.1 eq.) of triethylamine in 15 mL of dry toluene under an argon atmosphere. After 12 hours the reaction mixture was stirred at 80° C. for 3 hours. The mixture was cooled to ambient temperature and 143 mg (0.5 eq.) of 2,3,4,6-tetra-O-acetyl galaclose 12 ($R^5$=—Ac, $R^6$=—$CH_2OAc$) was added. The course of the reaction was followed by means of TLC ($SiO_2$—$Et_2O$). After the galactose 12 had disappeared, the reaction mixture was diluted with 200 mL of diethylether and washed with 100 mL portions of aqueous 0.5N potassium bisulfate (twice), demineralized water, saturated aqueous sodium bicarbonate and brine succesively. The organic layer was dried over anhydrous sodium sulfate and evaporated. The residual oil was purified by means of column chromatography ($SiO_2$—$Et_2O$/hexane 2/1) to yield 196 mg of N-[4-(tert-butyldimethylsilyloxymethyl)phenyl] O-(2,3,4,6-tetra-O-acetyl β-galactosyl) carbamate 13 ($R^3$=—H, $R^5$=—Ac, $R^6$=—$CH_2OAc$), 78% from 12, as a white foam.

N-[4-(hydroxymethyl)phenyl] O-(2,3,4,6-tri-O-acetyl β-galactosyl) carbamate 14 ($R^3$=—H, $R^5$=—Ac, $R^6$=—$CH_2OAc$)

180 mg (0.29 mmol) of 13 ($R^3$=—H, $R^5$=—Ac, $R^6$=—$CH_2OAc$) was stirred in 30 mL of tetrahydrofuran/demineralized water/acetic acid 1/1/1. The course of the deprotection reaction was followed by TLC ($SiO_2$ $Et_2O$). After no starting material could be detected, the reaction mixture was deluted with 200 mL of methylene chloride and washed with 100 mL portions of demineralized water (3 times), aqueous saturated sodium bicarbonate and with brine succesively. The organic layer was dried over anhydrous sodium sulfate and evaporated. The tert-butyldimethylsilanol in the reaction mixture was removed under reduced pressure (0.1 mm Hg) to afford 125 mg of N4-(hydroxymethyl)phenyl O-(2,3,4,6-tetra-O-acetyl β-galactosyl) carbamate 14 ($R^3$=—H, $R^5$=—Ac, $R^6$=—$CH_2OAc$), 87%.

N-[4-(daunorubicin-N-carbonyl-oxymethyl)phenyl] O-(2,3,4,6-tetra-O-acetyl β-galactosyl) carbamate 17 ($R^1$=—OMe, $R^2$=—H, $R^3$=—H, $R^5$=—Ac, $R^6$=—$CH_2OAc$)

50 mg (0.10 mmol) of 14 ($R^3$=—H, $R^5$=—Ac, $R^6$=$CH_2OAc$) was stirred with 19 mg (1.05 eq.) of N-succinimidyl chloroformate 15 and 10 µL (1.2 eq.) of anhydrous pyridine in 5 mL of anhydrous methylene chloride. After no starting material could be detected (TLC $SiO_2$ $Et_2O$), a solution of 68 mg (1.2 eq.) daunorubicin-HCl 16 ($R^1$=—OMe, $R^2$=—H) and 35 µL (2 eq.) of diisopropyl ethyl amine in 15 mL of dry N,N-dimethyl formamide were added. The course of the reaction was monitorred by TLC ($SiO_2$—$CH_2Cl_2$/EtOH 10/1). After all of the active ester starting material had disappeared, the reaction mixture was diluted with 200 mL of methylene chloride and washed with 100 mL portions of aqueous 0.5N potassium bisulfate (3 times), demineralized water, aqueous saturated sodium bicarbonate (twice) and with brine. The organic layer was dried over anhydrous sodium sulfate and evaporated. The resulting red residue was purified twice by means of circular chromatography using a chromatotron supplied with a 2 mm silica plate using methylene chloride/ethanol 20/1 as eluent. After evaporation of the eluent, the resulting red product was sonicated in diisopropyl ether and filtrated to yield 75 mg of N-[4-(daunorubicin-N-carbonyl-oxymethyl)phenyl] O-(2,3,4,6-tetra-O-acetyl β-galactosyl) carbamate 17 ($R^1$=—OMe, $R^2$=—H, $R^3$=—H, $R^5$=—Ac, $R^6$=—$CH_2OAc$), 71% as amorphous red crystals.

N-[4-(daunorubicin-N-carbonyl-oxymethyl)phenyl] O-β-galactosyl carbamate 1f-para ($R^1$=—OMe, $R^2$=—H, $R^3$=—H, $R^4$=—$CH_2OH$)

50 mg (0.048 mmol) of 17 ($R^1$=—OMe, $R^2$=—H, $R^3$=—H, $R^5$=—Ac, $R^6$=—$CH_2OAc$) was dissolved in 2.29 mL (6 eq.) of a 0.125N lithium hydroxyde solution in methanol/demineralized water 3/1 and cooled to 0° C. The resulting deep blue solution was stirred at 0° C. under an argon atmosphere. Progress of the deproteetion was monitorred on reversed phase TLC ($SiO_2$—$C_{18}$ MeCN/$H_2O$ 1/1). After completion of the reaction, the reaction mixture was diluted with 5 mL of demineralized water and neutralized by adding ca. 2 g of amberlite cation exchange material ($H^+$ form). The amberlite is removed by filtration and the red aqueous product solution was transferred to a reversed phase column packed with RP-$C_{18}$ material and eluted with 300 mL of demineralized water to remove impurities. The column was succesively washed with 20 mL of acetonitrile/demineralized water 1/1 to elute the product and the acetonitrile was removed by evaporation. Freeze drying of the aqueous product solution afforded 31 mg of N-[4-(daunorubicin-N-carbonyl-oxymethyl)phenyl]O-β-galactosyl carbamate 1f-para ($R^1$=—OMe, $R^2$=—H, $R^3$=—H, $R^4$=—$CH_2OH$), 73% as a red fluffy solid.

EXAMPLE 8

Serum Stability

The prodrugs of examples 1 to 7 in human serum or in phoshate buffer showed no parent drug formation after 24 hours of incubation at 37° C., as analyzed by HPLC using a silica $C_{18}$ column and an isocratic eluent which consisted of 2 mM triethylamine in 20 mM $NaH_2PO_4$ (pH=4.0)/ acetonitrile (2/1, v/v).

EXAMPLE 9

Anti-proliferative Effect

The anti-proliferative effect of daunorubicin, doxorubicin and idarubicin, and of the prodrugs of examples 1 to 6 on OVCAR-3 cells was determined by measuring cell growth with a protein dye stain (H. J. Haisma et al. Br. J. Cancer 1992, 66, 474–478. Cells were harvested with 0.25 trypsin and 0.2% EDTA in PBS to obtain a single cell suspension and seeded in 96-wells tissue culture plates ($2\times10^6$ cells/mL 10 µL/well, 3 wells per concentration). Drug or prodrug was added (10 µL/well) at different concentrations with a range of 3 or more logs. After incubation for 24 hours, 200 µL of culture medium (supplemented DMEM) was added and the cells were grown for another 72 hours. Cells were fixed with 25% trichloroacetic acid for 1 hour at 4° C. and washed with water. After staining the cells with 0.4% sulforhodamine B in 1% (v/v) acetic acid for 15 min. at room temperature, they were washed with 1% acetic acid and air-dried. The bound dye was solubilized with 10 mM unbuffered Tris and the absorbance was read at 492 nm. The absorbance was linear with cell concentrations from 1,000 to 200,000 cells/well. Separate wells were fixed 24 hours after seeding to substract background staining. The anti-proliferative effects were determined and expressed as $IC_{50}$ values which are the (pro)drug concentrations that gave 50% growth inhibition when compared to control cell growth.

| compound | $R^1$ | $R^2$ | $R^3$ | $R^4$ | $IC_{50}$ (µM) | parent drug |
|---|---|---|---|---|---|---|
| 1a-para | —OMe | —H | —H | —C(O)ONa | 22 | daunorubicin |
| 1a-ortho | —OMe | —H | —H | —C(O)ONa | 20 | daunorubicin |
| 1b-para | —OMe | —OH | —H | —C(O)ONa | >10 | doxorubicin |
| 1c-para | —H | —H | —H | —C(O)ONa | >1 | idarubicin |
| 1d-para | —OMe | —H | —H | —CH$_2$OH | 20 | daunorubicin |
| 12a | —OMe | —OMe | —OMe | —C(O)ONa | 1.2 | daunorubicin |
| 12b | —OMe | —OMe | —OMe | —C(O)ONa | 1.0 | doxorubicin |
| 12c | —OMe | —OMe | —OMe | —C(O)ONa | 0.1 | idarubicin |

EXAMPLE 10

Enzyme Hydrolysis Half-lifes

Half-lifes of enzyme hydrolysis were determined by incubating 100 µM prodrug at pH =6.8 with 0.03 U/mL β-glucuronidase or 0.3 U/mL β-glucosidase or β-galactosidase at 37° C.

| compound | R1 | $R^2$ | R3 | R4 | enzyme | $T_{1/2}$ (min.) | parent drug |
|---|---|---|---|---|---|---|---|
| 1a-para | —OMe | —H | —H | —C(O)ONa | β-glucuronidase | 135 | daunorubicin |
| 1a-ortho | —OMe | —H | —H | —C(O)ONa | β-glucuronidase | 125 | daunorubicin |
| 1b-para | —OMe | —OH | —H | —C(O)ONa | β-glucuronidase | 170 | doxorubicin |
| 1c-para | —H | —H | —H | —C(O)ONa | β-glucuronidase | 120 | idarubicin |
| 1d-para | —OMe | —H | —H | —CH$_2$OH | β-glucosidase | >500 | daunorubicin |

What is claimed is:

1. An anthracycline derivative coupled to an enzymatically clearable N-phenyl-O-glycosyl carbamate space group, said anthracycline derivative having formula 1

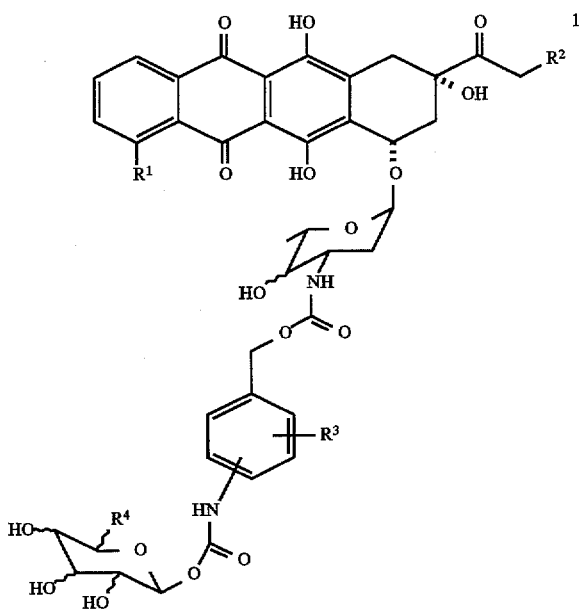

wherein
R¹=—H, —OH or —OMe
R²=—H or —OH
R³=—H, —CX₃, —NO₂, —CN, —X, —Y, —OY, —NHY —S(O₂)Y, C(O)Y or C(O)OY
R⁴=CH₂OH or C(O)O—Z⁺
X=halogen
Y=C₁–C₃ alkyl or aryl
Z=H, Li, Na or K
or an acid addition salt thereof.

2. An anti-tumor composition for administration orally, topically or by injection, containing as active ingredient an anthracycline derivative of formula 1:

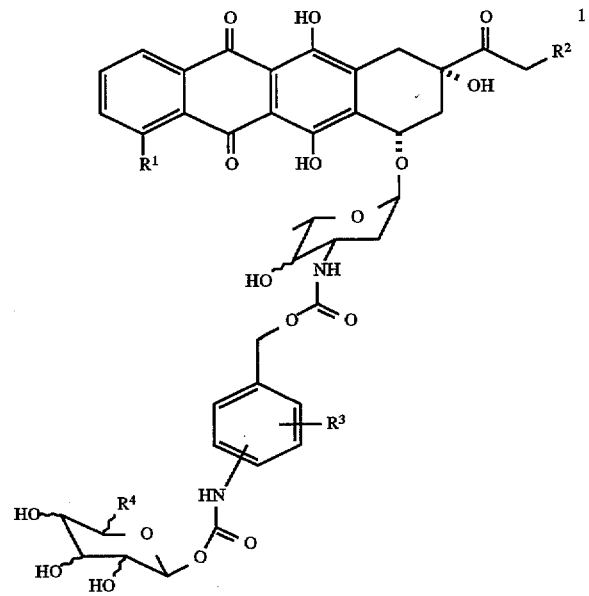

wherein

R¹=—H, —OH or —OMe

R²=—H or —OH

R³=—H, —CX₃, —NO₂, —CN, —X, —Y, —OY, —NHY —S(O₂)Y, C(O)Y or C(O)OY

R⁴=CH₂OH or C(O)O⁻Z⁺

X=halogen

Y=C₁–C₃ alkyl or aryl

Z=H, Li, Na, or K or an acid addition salt thereof, and a pharmaceutically acceptable carrier.

3. A process of synthesizing an anthracycline derivative having formula 1 according to claim 1, comprising the reaction of a compound having formula 14 or 21

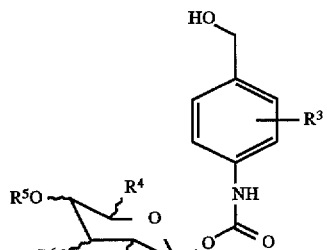

wherein R⁵ is —Ac and R⁶ is —CH₂OAc or C(O)OMe, with a compound having formula 16

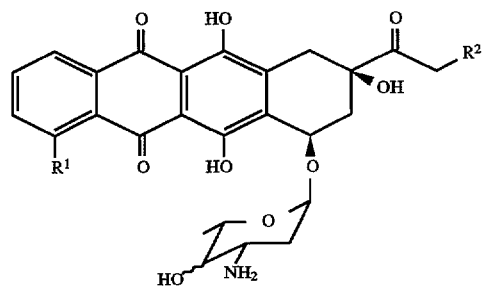

wherein R¹ is —H , —OH or —OMe and R² is —H or —OH, in the presence of N-succinimidyl chloroformate or p-nitrophenyl chloroformate to obtain a compound having formula 17 or 22 respectively;

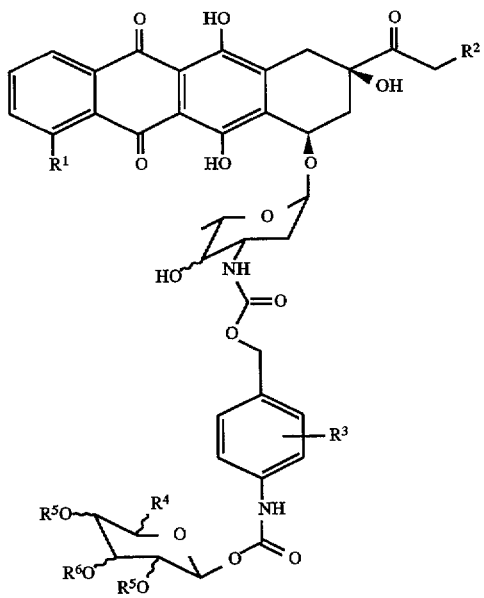

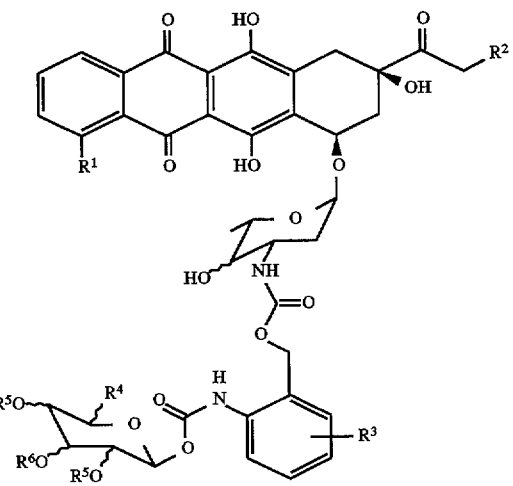

followed by the deprotection of the carbohydrate moiety, to obtain a derivative having formula 1.

4. A process according to claim 3 wherein a compound having formula 14 or 21,

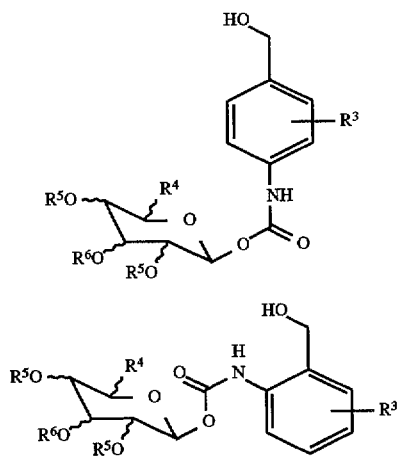

is obtained by reaction of a compound having formula

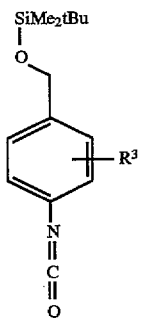

wherein $R^3$ is defined as above, with an anomerically unprotected carbohydrate having formula 12,

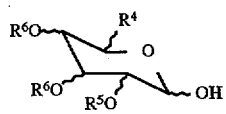

wherein $R^5$ and $R^6$ are defined as above, to obtain a carbamate having formula 13 or 20 respectively

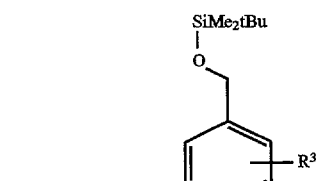

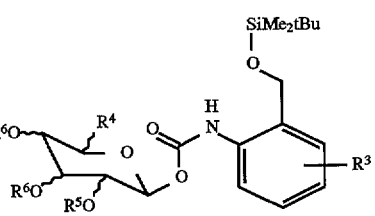

followed by deprotection of the silyl protective group to obtain a compound having formula 14 or 21 respectively.

5. A process according to claim 3 wherein a compound having formula 14 or 21, is obtained by reaction of a compound having formula 24 or 28

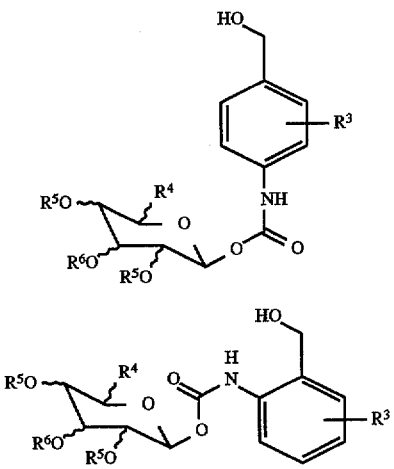

with an anomerically unprotected carbohydrate having formula 12,

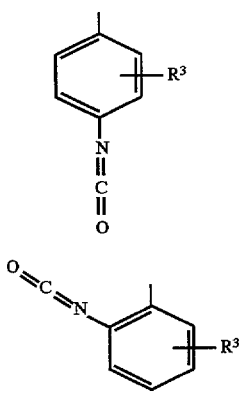

in presence of toluene to obtain a carbamate having formula 25 or 29 respectively,

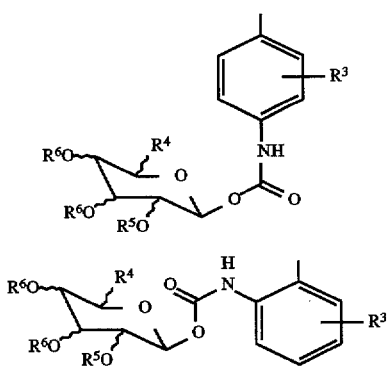

followed by bromination leading to compounds having formulae 26 and 30 respectively,

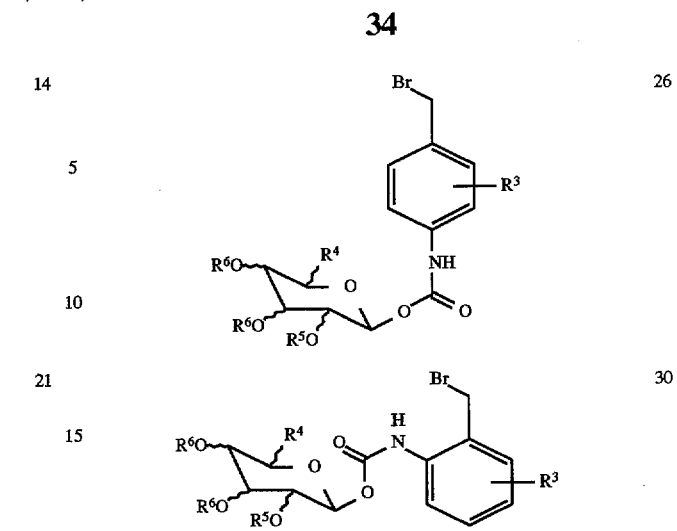

and conversion of the bromine to a hydroxyl group to obtain a compound having formula 14 or 21 respectively.

6. A process according to claim 4, wherein a compound having formula 11 or 19, is obtained by reaction of a compound having formula 10 or 18 respectively

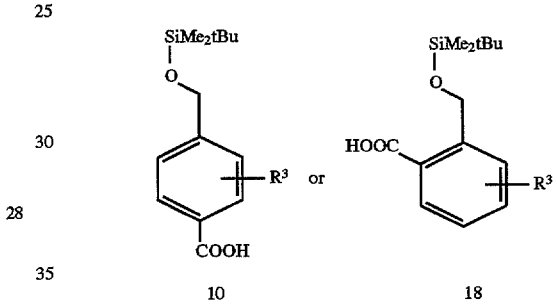

with diphosphoryl azide.

7. A process according to claim 6, wherein a compound having formula 24 or 28, is obtained by reaction of a compound having formula 23 or 27 respectively

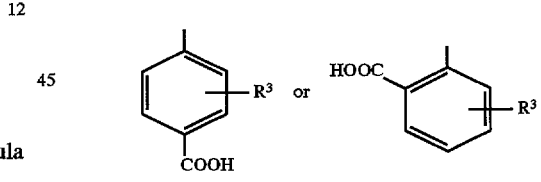

with diphenylphosphoryl azide.

8. In a method for the treatment of tumors comprising administering an antibody directed enzyme prodrug to a patient in need of said therapy, wherein an antibody targets an enzyme to a tumor site, the improvement wherein said antibody directed enzyme prodrug is an antharcycline compound of formula 1 according to claim 1, wherein said prodrug passes to the tumor site and said prodrug is converted at the tumor site by an enzyme to a cytotoxic compound, said compound of formula 1 being administered in an amount sufficient to be converted at said tumor site to an anti-tumor-effective amount of said cytotoxic compound.

9. A process according to claim 4 wherein a compound having formula 14 or 21,

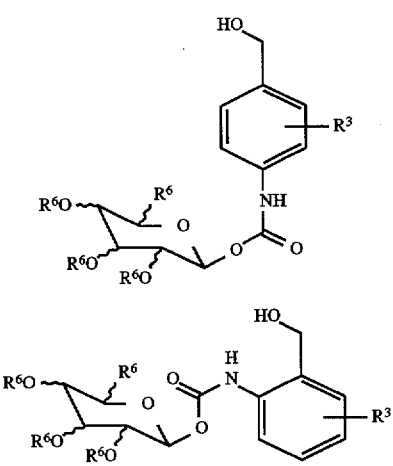

is obtained by reaction of a compound having formula 24 or 28

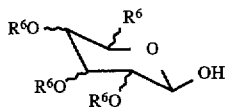

with an anomerically unprotected carbohydrate having formula 12, in the presence of toluene to obtain a carbamate having formula 25 or 29 respectively,

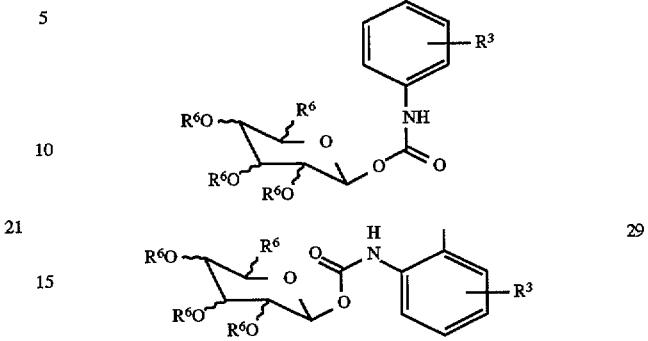

followed by bromination leading to compounds having formulae 26 and 30 respectively,

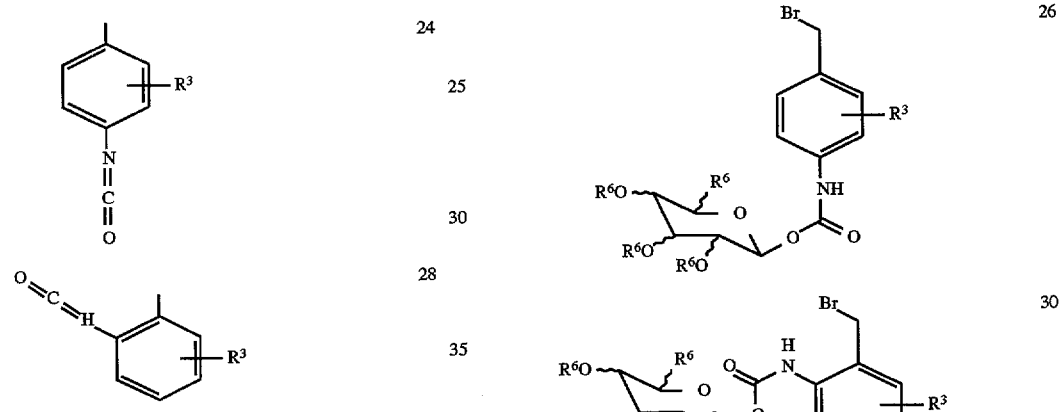

and conversion of the bromine to a hydroxyl group to obtain a compound having formula 14 or 21 respectively.

* * * * *